(12) United States Patent
Vellinger et al.

(10) Patent No.: US 11,788,042 B2
(45) Date of Patent: Oct. 17, 2023

(54) BIOMANUFACTURING SYSTEM, METHOD, AND 3D BIOPRINTING HARDWARE IN A REDUCED GRAVITY ENVIRONMENT

(71) Applicant: Techshot, Inc., Greenville, IN (US)

(72) Inventors: John C. Vellinger, Floyds Knobs, IN (US); Eugene Boland, Louisville, KY (US); Michael A. Kurk, Georgetown, IN (US); Krystal Milliner, Georgetown, IN (US); Nester Samuel Logan, Greenville, IN (US); Carlos Chang, Greenville, IN (US)

(73) Assignee: REDWIRE SPACE TECHNOLOGIES, INC., Jacksonville, FL (US)

( * ) Notice: Subject to any disclaimer, the term of this patent is extended or adjusted under 35 U.S.C. 154(b) by 1042 days.

(21) Appl. No.: 16/517,106

(22) Filed: Jul. 19, 2019

(65) Prior Publication Data

US 2020/0010788 A1 Jan. 9, 2020

Related U.S. Application Data

(63) Continuation-in-part of application No. 15/225,547, filed on Aug. 1, 2016, now Pat. No. 10,655,096.

(Continued)

(51) Int. Cl.
*C12M 3/00* (2006.01)
*C12M 1/00* (2006.01)
(Continued)

(52) U.S. Cl.
CPC .......... *C12M 21/08* (2013.01); *B29C 64/364* (2017.08); *B33Y 30/00* (2014.12); *B33Y 40/00* (2014.12);
(Continued)

(58) Field of Classification Search
None
See application file for complete search history.

(56) References Cited

U.S. PATENT DOCUMENTS

| 7,198,940 B2 | 4/2007 | Vellinger et al. |
| 9,656,426 B2 | 5/2017 | Snyder et al. |

(Continued)

FOREIGN PATENT DOCUMENTS

| CA | 2924078 A1 | 4/2015 |
| CA | 2962090 A1 | 3/2016 |

(Continued)

OTHER PUBLICATIONS

Wong, JY et al. 3D printing of surgical instruments for long-duration space missions. Aviation, Space, and Environmental Medicine. Jul. 2014. 85(7): 758-763. Publication date: Jul. 1, 2014 (Year: 2014).

(Continued)

*Primary Examiner* — Holly Kipouros
(74) *Attorney, Agent, or Firm* — Terry M. Sanks, Esq.; Beusse Sanks, PLLC

(57) ABSTRACT

A method, apparatus, and system are provided for the printing and maturation of living tissue in an Earth-referenced reduced gravity environment such as that found on a spacecraft or on other celestial bodies. The printing may be three-dimensional structures. The printed structures may be manufactured from low viscosity biomaterials.

13 Claims, 15 Drawing Sheets

Related U.S. Application Data

(60) Provisional application No. 62/199,793, filed on Jul. 31, 2015.

(51) Int. Cl.

| | | |
|---|---|---|
| *B33Y 30/00* | (2015.01) | |
| *B33Y 40/00* | (2020.01) | |
| *C12M 1/42* | (2006.01) | |
| *C12M 1/26* | (2006.01) | |
| *B29C 64/10* | (2017.01) | |
| *B33Y 10/00* | (2015.01) | |
| *B29C 64/364* | (2017.01) | |
| *C12N 1/04* | (2006.01) | |

(52) U.S. Cl.
CPC ............ *C12M 23/40* (2013.01); *C12M 29/10* (2013.01); *C12M 33/00* (2013.01); *C12M 35/02* (2013.01); *B29C 64/10* (2017.08); *B33Y 10/00* (2014.12); *C12M 35/04* (2013.01); *C12N 1/04* (2013.01)

(56) References Cited

U.S. PATENT DOCUMENTS

| | | |
|---|---|---|
| 9,764,515 B2 | 9/2017 | Tost et al. |
| 9,802,355 B2 | 10/2017 | Snyder |
| 10,052,820 B2 | 8/2018 | Kemmer et al. |
| 10,086,568 B2 | 10/2018 | Snyder et al. |
| 10,655,096 B2 | 5/2020 | Vellinger |
| 10,851,333 B2 | 12/2020 | Vellinger |
| 2002/0115196 A1* | 8/2002 | Boven ............... C12M 41/46 435/287.1 |
| 2009/0263849 A1 | 10/2009 | Sun et al. |
| 2010/0055299 A1 | 3/2010 | Church et al. |
| 2010/0248343 A1* | 9/2010 | Aten ............... C12M 35/02 435/283.1 |
| 2011/0237002 A1 | 9/2011 | Church et al. |
| 2012/0035742 A1* | 2/2012 | Vunjak-Novakovic ............... A61F 2/30942 435/174 |
| 2013/0017564 A1 | 1/2013 | Guillemot |
| 2014/0012407 A1* | 1/2014 | Murphy ............... B41J 2/04526 700/119 |
| 2014/0038258 A1* | 2/2014 | Akra ............... C12M 35/02 435/297.1 |
| 2015/0037445 A1 | 2/2015 | Murphy et al. |
| 2015/0108687 A1 | 4/2015 | Snyder |
| 2015/0112472 A1 | 4/2015 | Chen et al. |
| 2015/0144284 A1 | 5/2015 | Snyder et al. |
| 2015/0210408 A1 | 7/2015 | Dunn et al. |
| 2015/0298123 A1* | 10/2015 | Block, III ............ F04B 43/0054 435/284.1 |
| 2015/0375453 A1 | 12/2015 | Yost et al. |
| 2016/0032234 A1* | 2/2016 | Rosell Ferrer ......... C12M 35/04 435/283.1 |
| 2016/0068793 A1* | 3/2016 | Maggiore ............. B29C 64/232 901/22 |
| 2016/0082652 A1 | 3/2016 | Snyder et al. |
| 2016/0101463 A1 | 4/2016 | Snyder et al. |
| 2016/0221265 A1 | 8/2016 | Snyder et al. |
| 2016/0243759 A1 | 8/2016 | Snyder et al. |
| 2016/0282338 A1 | 9/2016 | Miklas et al. |
| 2016/0288414 A1 | 10/2016 | Ozbolat et al. |
| 2017/0029765 A1 | 2/2017 | Vellinger et al. |
| 2017/0036783 A1 | 2/2017 | Snyder |
| 2017/0175066 A1* | 6/2017 | Olsen .................. A61J 1/12 |
| 2018/0087016 A1* | 3/2018 | Rios .................. G02B 21/0004 |
| 2018/0163162 A1 | 6/2018 | Vellinger |
| 2020/0208117 A1* | 7/2020 | Tresoldi ............. G01N 33/5082 |
| 2020/0347333 A1 | 11/2020 | Vellinger |
| 2020/0353691 A1* | 11/2020 | Martinez ................ C12M 33/00 |
| 2020/0384690 A1* | 12/2020 | Myers .................... B33Y 80/00 |
| 2021/0071127 A1* | 3/2021 | Levy .................... C12N 5/0667 |
| 2021/0139827 A1 | 5/2021 | Vellinger |

FOREIGN PATENT DOCUMENTS

| | | |
|---|---|---|
| CA | 2994277 A1 | 4/2017 |
| CN | 107921564 A | 4/2018 |
| EP | 3027389 A1 | 6/2016 |
| EP | 3147106 A1 | 3/2017 |
| EP | 3238916 A1 | 11/2017 |
| WO | 2012022351 A1 | 2/2012 |
| WO | 2016044837 A1 | 3/2016 |
| WO | 2017023865 | 2/2017 |
| WO | 2017069832 A2 | 4/2017 |

OTHER PUBLICATIONS

Serway, RA and JS Faughn. College Physics, 4th edition (New York, Saunders College Publishing, 1995), pp. 44, 45, and back cover (Year: 1995).

European Patent Office, International Search Report and Written Opinion of PCT/US16/45040, 13 pages, dated Nov. 8, 2016.

Fabrizio Bensch, Reuters: "World's first 3D-bioprinted transplant-ready organ to be unveiled in early 2015", Nov. 4, 2014 (Nov. 4, 2014), XP002763243 Retrieved from the Internet: URL:https://ww.rt.com/news/202175-3d-bioprinted-organ-transplatn/ [retrieved on Oct. 20, 2016] Nov. 4, 2015.

M. Moody: "3D Bioprinted Thyroid Gland by 2015, Kidney by 2018, Says Russian Scientists", Nov. 9, 2014 (Nov. 9, 2014), XP002763244, Retrieved from the Internet: URL:https://3dprint.com/23805/bioprinted-throid-kidney/ [retrieved on Oct. 20, 2016] Nov. 9, 2014.

Sandford Gary L et al: "Three-dimensional growth of endothelial cells in the microgravity-based rotating wall vessel bioreactor", In Vitro Cellular & Development Biolagy, Animal, Springer US, New York, vol. 38, No. 9, Oct. 1, 2001 (Oct. 1, 2001), pp. 493-504, XP009144922, ISSN: 1071-2690 Oct. 1, 2001.

Rodrigo A Rezende et al: "Development of a Bioreactor by Computer Fluid Dynamics Simulations for the Maturation of 3D Printed Organs by Rapid Prototyping", Chemical Engineering Transactions, Jan. 1, 2013 (Jan. 1, 2013), pp. 1153-1158, XP055312926, Retrieved from the Internet: URL:http://www.aidic.it/cet/13/32/193.pdf [retrieved on Oct. 21, 2016] Jan. 1, 2013.

Sean V Murphy et al: "3D bioprinting of tissues and organs", Nature Biotechnology, vol. 32, No. 8, Aug. 5, 2014 (Aug. 5, 2014), pp. 773-785, XP055244641, US ISSN: 1087-0156, DOI: 10.1038/nbt.2958 Aug. 5, 2014.

Facility' definition. The Oxford English Dictionary. Third Edition, Sep. 2009.

\* cited by examiner

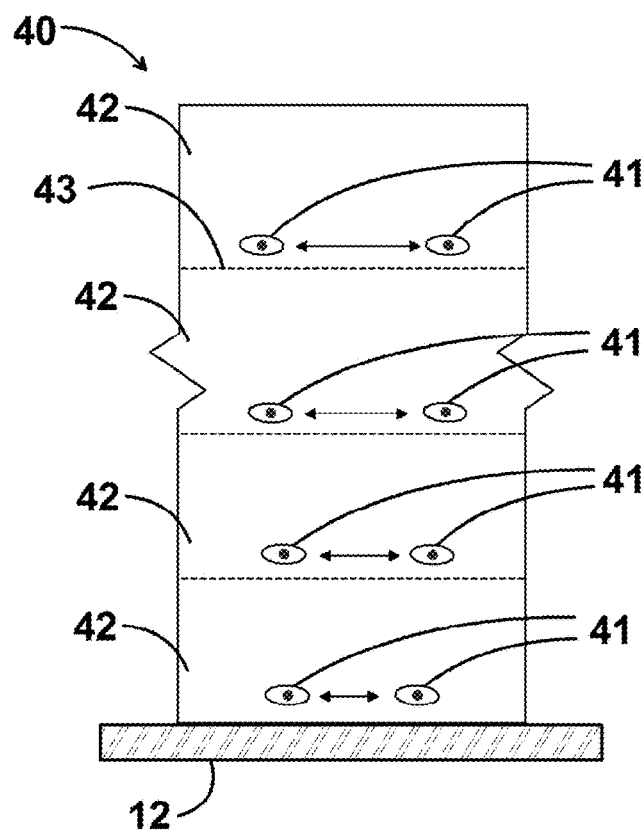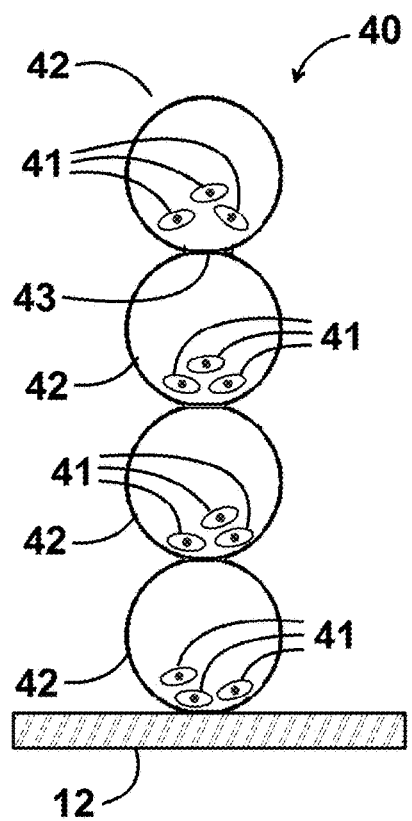
FIG. 8A
PRIOR ART
FIG. 8B
PRIOR ART

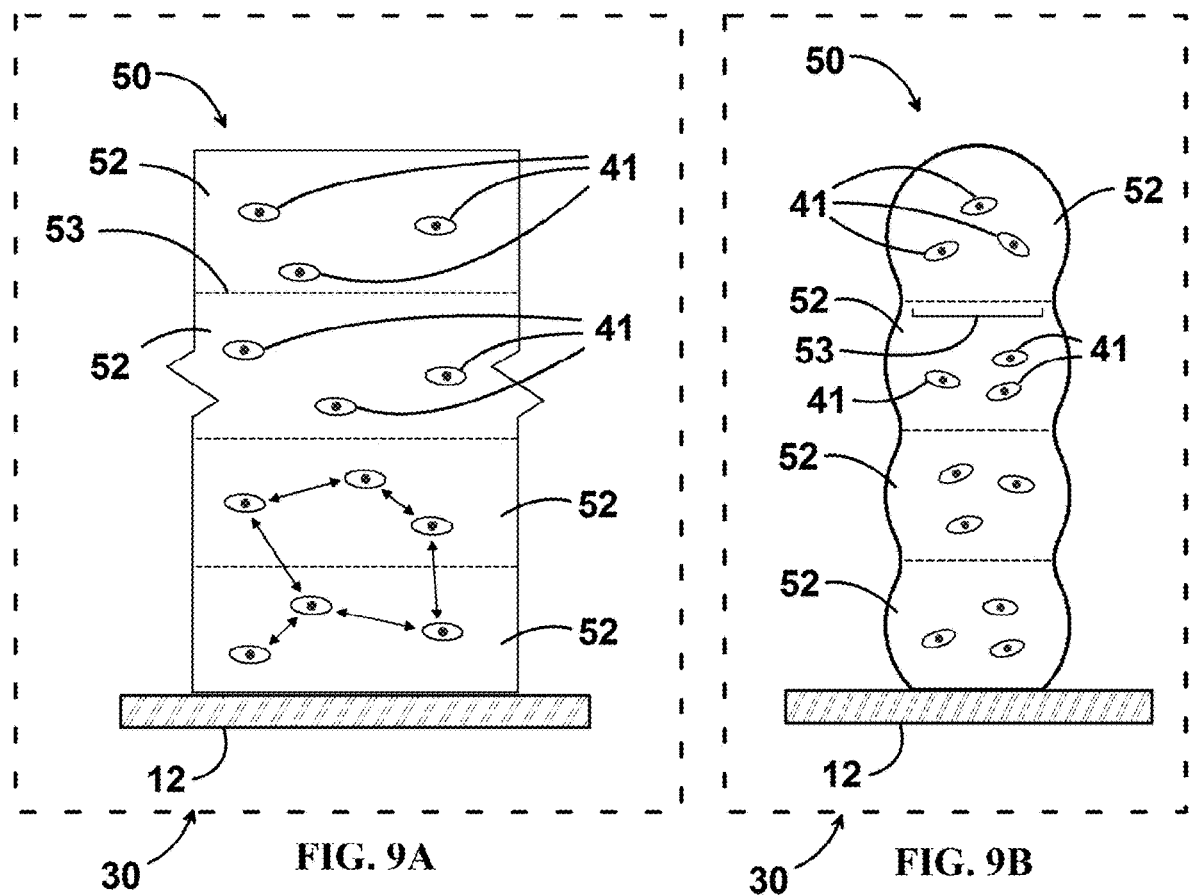

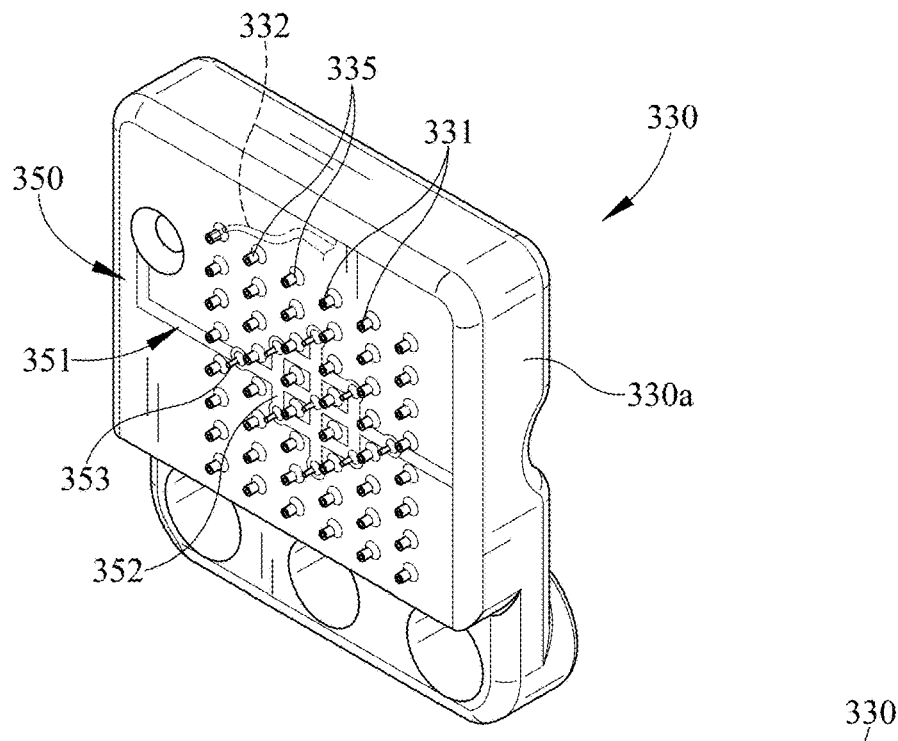
FIG. 13
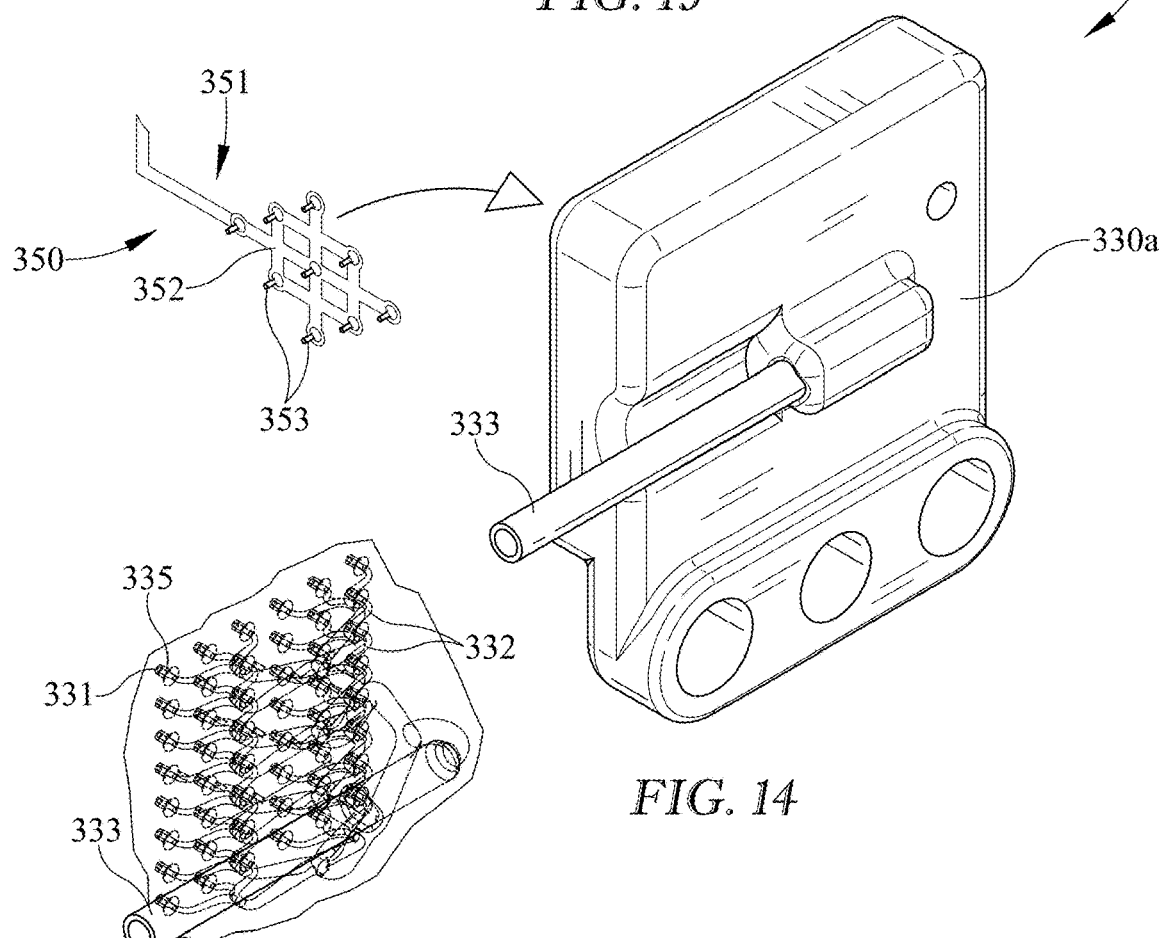
FIG. 14
FIG. 14a

US 11,788,042 B2

BIOMANUFACTURING SYSTEM, METHOD, AND 3D BIOPRINTING HARDWARE IN A REDUCED GRAVITY ENVIRONMENT

CROSS-REFERENCE TO RELATED APPLICATIONS

This application is a continuation-in-part patent application of and claims priority and benefit under 35 U.S.C. § 120 to copending U.S. patent application Ser. No. 15/225,547 filed on Aug. 1, 2016, which claims priority to U.S. Provisional App. No. 62/199,793, filed on Jul. 31, 2015, the entire contents of all of the forgoing are incorporated by reference in their entirety.

BACKGROUND

The present embodiments relate to a system, method, and apparatus for bioprinting in a reduced gravity environment.

SUMMARY

In some embodiments, a method for the additive manufacturing of living tissue in a reduced gravity environment may comprise one or more of the steps of providing a reduced gravity environment, providing a housing having a bioprinter, providing one or more bioinks, and printing one or more three-dimensional tissues with the one or more bioinks from said bioprinter within the reduced gravity environment. One or more three-dimensional tissues may be printed in a bioreactor. In use, the bioreactor may be positioned on at least one print stage of the bioprinter. Another step may include positioning the one or more three-dimensional tissues into a bioreactor after printing. The one or more three-dimensional tissues may be positioned into the bioreactor manually or automatically. Further one or more bioinks may include non-living biological components such as at least one of natural or synthetic structural proteins, polymers, macromolecules, or pharmaceuticals. The reduced gravity environment may be an environment wherein the gravitational acceleration is less than 9.807 meters per second per second. In addition, one or more bioinks may include living biological components such as at least one of undifferentiated stem cells, partially differentiated stem cells, terminally differentiated cells, microvascular fragments, or organelles.

In addition, in some embodiments, the method may include the step of maturing one or more three-dimensional tissues. The one or more bioinks may have a viscosity range of approximately 1 to 10,000,000 centipoise, preferably the viscosity range is approximately 5 to 2,000 centipoise. Another step may include controlling at least one of temperature or humidity. Further steps may include providing one or more print stages and controlling the thermal characteristics of the one or more print stages.

In some embodiments, further steps may provide one or more print heads and controlling the thermal characteristics of the one or more print heads. There may be additional steps of controlling the temperature of one or more bioinks. Additional steps of at least partially controlling the additive manufacturing of living tissue in the reduced gravity environment from one or more locations may be used. The one location may be terrestrial. The one or more three-dimensional tissues may be transported from the reduced gravity environment to a different gravity environment. The different gravity environment may be at least one of a terrestrial environment or an extraterrestrial environment. Another embodiment may include the step of incorporating prefabricated structure into one or more three dimensional tissues for at least one of the creation of the tissue or organ, support structure, perfusion aid, implantation aid, cell delivery, or reagent delivery.

In some embodiments, a biomanufacturing system capable of assembling and maturing living tissue in a reduced gravity environment from one or more bioinks may include a bioprinter, a cell culturing device, one or more bioinks, and an environment of reduced gravity surrounding the bioprinter and the cell culturing device. The bioprinter may be a three dimensional printer. Further the bioprinter may be separate from the cell culturing device. The cell culturing device may include at least one of a mechanical tissue stimulation or electrical tissue stimulation.

In addition, in some embodiments, one or more print heads of the bioprinter may be in fluid communication with the interior of the cell culturing device. Further the environment of reduced gravity may be temperature controlled and/or humidity controlled. In addition, one or more bioinks may have a viscosity range of approximately 1 to 10,000,000 centipoise, preferably the viscosity range is approximately 5 to 2,000 centipoise. The environment of reduced gravity may have a gravitational acceleration less than 9.807 meters per second per second. Further in some embodiments, at least one of the cell culturing device or the one or more bioinks downstream of the bioprinter may be transported from the environment of reduced gravity to an environment having a different gravity. In some embodiments, the system is a modular configuration. The modular configuration may include both major systems and some individual components that may be swapped-out for resupply, refurbishment, or upgrade. The modular configuration may include one or more of captive fasteners, self-aligning blind-mate electrical and mechanical connectors, grouping of low mean time between failure (MTBF) and high MTBF components, grouping of certain electrical components within electromagnetic interference shielding, and/or colocation of elements requiring air or liquid cooling. In addition, the cell culturing device may include an integrated life support system for transportation of living tissue from said environment of reduced gravity to an environment having a different gravity.

Further, in some embodiments, an additive manufacturing apparatus may include a reduced gravity environment, a bioprinter positioned in the reduced gravity environment such that the bioprinter has one or more print heads in relation to at least one print stage, and one or more bioinks have a viscosity range of approximately 1 to 10,000,000 centipoise in fluid communication with the one or more print heads. The bioprinter may be a three-dimensional printer.

In addition, in some embodiments, the apparatus may have a bioink dispensing system, a visualization system capable of observing a top surface of the print stage, an x-axis translation system, a y-axis translation system, and a z-axis translation system, and wherein at least one of the one or more print heads allow direct write constant pressure extrusion. Further embodiments may include one or more bioreactors. The viscosity range may be approximately 5 to 2,000 centipoise. In addition, one or more thermoplastics may be in fluid communication with the one or more print heads. Further the housing may have at least one of temperature control or humidity control. In some embodiments the apparatus is a modular configuration. The modular configuration may include both major systems and some individual components that may be swapped-out for resupply, refurbishment, or upgrade. The modular configuration may include one or more of captive fasteners, self-aligning blind-mate electrical and mechanical connectors, grouping of low mean time between failure (MTBF) and high MTBF components, grouping of certain electrical components within electromagnetic interference shielding, and/or colocation of elements requiring air or liquid cooling.

In some embodiments, a bioreactor for receiving a printed tissue may comprise a housing defining a volume therein. In various embodiments, the bioreactor may include a print platform within the volume of the housing. In some embodiments, the bioreactor may include an intake manifold and an outlet manifold positioned in the volume of the housing. In various embodiments, each one of the intake manifold and the outlet manifold includes one or more ports adapted to be in fluid communication with a printed tissue within the housing.

In addition, in some embodiments, at least one of the intake manifold and the outlet manifold may include an electrical stimulation device. In various embodiments, the electrical stimulation device may include a conductive material positioned on one or more surfaces of the at least one of the intake manifold and the outlet manifold. In some embodiments, the conductive material may include one or more needles projecting and adapted to engage a printed tissue. In various embodiments, at least one of the intake manifold and the outlet manifold may include one or more needles defining the one or more ports. Moreover, in some embodiments, at least one of the intake manifold and the outlet manifold may include one or more channels in communication with the one or more ports. In various embodiments, at least one of the intake manifold and the outlet manifold may be moveable relative to each other. In some embodiments, the bioreactor may include a drive mechanism moving at least one of the intake manifold and the outlet manifold. In various embodiments, the bioreactor may include one or more air traps in fluid communication with the one or more ports. In some embodiments, the bioreactor may include one or more detachable feed bags and waste bags.

In various embodiments, a bioreactor for receiving a printed tissue may comprise a housing having one or more manifolds therein adapted to engage a printed tissue. In some embodiments, the one or more manifolds may have a plurality of perfusion ports in fluid communication a printed tissue. In various embodiments, the one or more manifolds may have one or more electrical stimulation devices. In some embodiments, the one or more manifolds may have a mechanical stimulation device connected thereto.

In addition, in various embodiments, at least one of the one or more manifolds may have one of the plurality of perfusion ports, the one or more electrical stimulation devices, and the mechanical stimulation device. In some embodiments, the bioreactor may include a print platform. In various embodiments, at least one of the one or more manifolds may contain the plurality of perfusion ports defined by one or more needles. In various embodiments, the mechanical stimulation device may move the one or more manifolds between a compressed position and an extended position. Moreover, in some embodiments, the one or more electrical stimulation devices may be an exterior coating to the one or more manifolds. In various embodiments, the exterior coating may include one or more needles. In some embodiments, the one or more manifolds may include an intake manifold and an outlet manifold.

In some embodiments, a method of culturing a printed tissue in a bioreactor in a reduced gravity environment may comprise the step of providing a reduced gravity environment. In various embodiments, the method may include providing one or more bioreactors in the reduced gravity environment. In some embodiments, the method may include printing one or more tissues into the one or more bioreactors. In various embodiments, the method may include providing one or more perfusions to one or more printed tissues. In some embodiments, the method may include providing one or more electrical stimulations to one or more printed tissues. Moreover, in some embodiments, the method may include providing one or more mechanical stimulations to one or more printed tissues.

In addition, in some embodiments, the method may include removing air from fluid communication within the one or more bioreactors. In various embodiments, the method may include engaging one or more manifolds with the one or more printed tissues. In some embodiments, the method may include fluidly engaging one or more of at least one of a feed bag and a waste bag to the one or more bioreactors. In various embodiments, the method of providing one or more perfusions to one or more printed tissues may include the step of passing fluid from an intake manifold through the one or more printed tissues to an outlet manifold. Moreover, in some embodiments, the method may include recirculating fluid between the intake manifold, the one or more printed tissues, and the outlet manifold.

In various embodiments, a method of culturing a printed tissue in a bioreactor in a reduced gravity environment may comprise the steps of providing a reduced gravity environment. In some embodiments, the method may include providing one or more bioreactors in the reduced gravity environment. In various embodiments, the method may include printing one or more tissues into the one or more bioreactors. In some embodiments, the method may include providing an intake manifold and an outlet manifold, each one of the intake manifold and the outlet manifold having one or more ports. In various embodiments, the method may include providing one or more perfusions to one or more printed tissues through the one or more ports of the intake manifold. In some embodiments, the method may include providing one or more electrical stimulations to one or more printed tissues by contact with at least one of the intake manifold and the outlet manifold. Moreover, in various embodiments, the method may include providing one or more mechanical stimulations to one or more printed tissues by moving at least one of the intake manifold and the outlet manifold.

In addition, in various embodiments, the method of providing one or more mechanical stimulations may include at least one of compression or extending by moving at least one of the intake manifold and the outlet manifold. In some embodiments, the method may include engaging at least one of the intake manifolds and the outlet manifold with the one or more printed tissues. In various embodiments, the method may include fluidly engaging the one or more ports of the intake manifold and the outlet manifold with one or more vessels within the one or more printed tissues. In some embodiments, the method of providing one or more perfusions to the one or more printed tissues may include a plurality of the one or more ports defined by a plurality of needles. In various embodiments, the method may include removing air from fluid communication within a housing within the one or more bioreactors. Moreover, in some embodiments, the method of printing one or more tissues into the one or more bioreactors may include the step of removing the one or more bioreactors from a 3D printer.

In some embodiments, a bioreactor for receiving a printed tissue may comprise a housing defining a volume therein. In various embodiments, the bioreactor may include a print platform within the volume of the housing. In some embodiments, the bioreactor my include an intake manifold and an outlet manifold positioned in the volume of the housing. In various embodiments, each one of the intake manifold and the outlet manifold may include one or more ports. Moreover, in some embodiments, the bioreactor may include at least one first air trap in fluid communication with the one or more ports of at least one of the intake manifold and the outlet manifold.

In addition, in some embodiments, at least one of the intake manifold and the outlet manifold includes an electrical stimulation device. In various embodiments, the bioreactor may include a second air trap. In some embodiments, the second air trap may be in fluid communication with the volume of the housing and a feed bag. In various embodiments, the bioreactor may include a waste bag in fluid communication with the volume of the housing. In some embodiments, the bioreactor may include a pump in fluid communication with the at least one first air trap. In various embodiments, at least one of the intake manifold and the outlet manifold may be moveable relative to each other.

In various embodiments, a bioreactor for receiving a printed tissue may comprise a housing having a volume, wherein the housing has one or more manifolds therein adapted to engage a printed tissue. In some embodiments, the one or more manifolds may have a plurality of perfusion ports. In various embodiments, the one or more manifolds may have one or more electrical stimulation devices. In some embodiments, the one or more manifolds may have a mechanical stimulation device connected thereto. In various embodiments, the bioreactor may include one or more air traps in fluid communication with the volume defined by the housing.

In addition, in various embodiments, at least one air trap may be in fluid communication with at least one of the plurality of perfusion ports of the one or more manifolds within the housing. In some embodiments, at least one of the one or more manifolds may have one of the plurality of perfusion ports, the one or more electrical stimulation devices, and the mechanical stimulation device. In various embodiments, the one or more manifolds may include an intake manifold and an outlet manifold. In some embodiments, one or more air traps may be in fluid communication with each one of the intake manifold and the outlet manifold. In various embodiments, one or more air traps may be in fluid communication with the volume of the housing and a feed bag. In some embodiments, at least one of the one or more manifolds may contain the plurality of perfusion ports defined by one or more needles. Moreover, in some embodiments, the mechanical stimulation device may move the one or more manifolds between a compressed position and an extended position.

In some embodiments, a method of culturing a printed tissue in a bioreactor in a reduced gravity environment may comprise the steps of providing a reduced gravity environment. In various embodiments, the method may include providing one or more bioreactors in the reduced gravity environment. In some embodiments, the method may include printing one or more tissues into the one or more bioreactors. In various embodiments, the method may include providing one or more perfusions to one or more printed tissues. Moreover, in some embodiments, the method may include removing air from the one or more bioreactors.

In addition, in some embodiments, the method may include one or more air traps in fluid communication with one or more manifolds. In various embodiments, the method of providing one or more perfusions to one or more printed tissues may include the step of recirculating fluid within the one or more bioreactors. In some embodiments, the method of removing air from the one or more bioreactors may occur during the step of recirculating fluid within the one or more bioreactors. In various embodiments, the method of removing air from the one or more bioreactors may include the step of priming one or more ports of one or more manifolds. In some embodiments, the method may include engaging the one or more manifolds to the printed tissue. In various embodiments, the method of removing air from the one or more bioreactors may include evacuating air from a volume defined by a housing of at least one of the one or more bioreactors. Moreover, in some embodiments, the method may include at least one of the steps of providing one or more electrical stimulations to the one or more printed tissues and providing one or more mechanical stimulations to the one or more printed tissues.

In various embodiments, a method of culturing a printed tissue in a bioreactor in a reduced gravity environment may comprise the steps of providing a reduced gravity environment. In some embodiments, the method may include providing a printed tissue in a housing of a bioreactor in the reduced gravity environment. In some embodiments, the method may include recirculating fluid to the printed tissue. Moreover, in various embodiments, the method may include removing air from the fluid recirculating to the printed tissue.

In addition, in various embodiments, the method may include supplying fluid from a feed bag to the housing. In some embodiments, the method may include removing air from the fluid communication of the feed bag to the housing. In various embodiments, the method may include priming one or more manifolds within the bioreactor with fluid. In various embodiments, the method may include engaging one or more manifolds with the printed tissue. In some embodiments, the method of recirculating fluid to the printed tissue may include recirculating fluid into one or more manifolds. In various embodiments, the method may include evacuating air from the housing. In some embodiments, the method may include printing the printed tissue in the housing of the bioreactor. In various embodiments, the method may include sealing the housing after the step of printing the printed tissue in the housing of the bioreactor. In some embodiments, the method may include at least one of the step of removing the bioreactor from a 3D bioprinter and printing a second printed tissue in a second bioreactor. Moreover, in some embodiments, the method may include at least one of the steps of providing one or more electrical stimulations to the printed tissue and providing one or more mechanical stimulations to the printed tissue.

These and other advantages and features, which characterize the embodiments, are set forth in the claims annexed hereto and form a further part hereof. However, for a better understanding of the embodiments, and of the advantages and objectives attained through its use, reference should be made to the Drawings, and to the accompanying descriptive matter, in which there is described example embodiments. This summary is merely provided to introduce a selection of concepts that are further described below in the detailed description, and is not intended to identify key or essential features of the claimed subject matter, nor is it intended to be used as an aid in limiting the scope of the claimed subject matter.

BRIEF DESCRIPTION OF THE FIGURES

In the drawings, like reference characters generally referred to the same parts throughout the different views.

Also, the drawings are not necessarily to scale, emphasis instead generally being placed upon illustrating the principles of the invention.

FIG. 8A is an enlarged side view of a portion of a prior art additive structure influenced by the negative effects of gravity.

FIG. 8B is a sectional view of the prior art additive structure of FIG. 8A influenced by the negative effects of gravity.

FIG. 9A is an enlarged side view of a portion of an embodiment of the additive structure printed in a reduced gravity environment.

FIG. 9B is a sectional view of the embodiment of the additive structure of FIG. 9A.

FIG. 13 is a perspective view of an embodiment of an intake manifold of the bioreactor of FIG. 10.

FIG. 14 is another perspective view of the intake manifold of FIG. 13 with the electrical stimulation device exploded therefrom.

FIG. 14a is a perspective view of the flow channels through the intake manifold of FIGS. 13 and 14.

DETAILED DESCRIPTION

Figure 1:
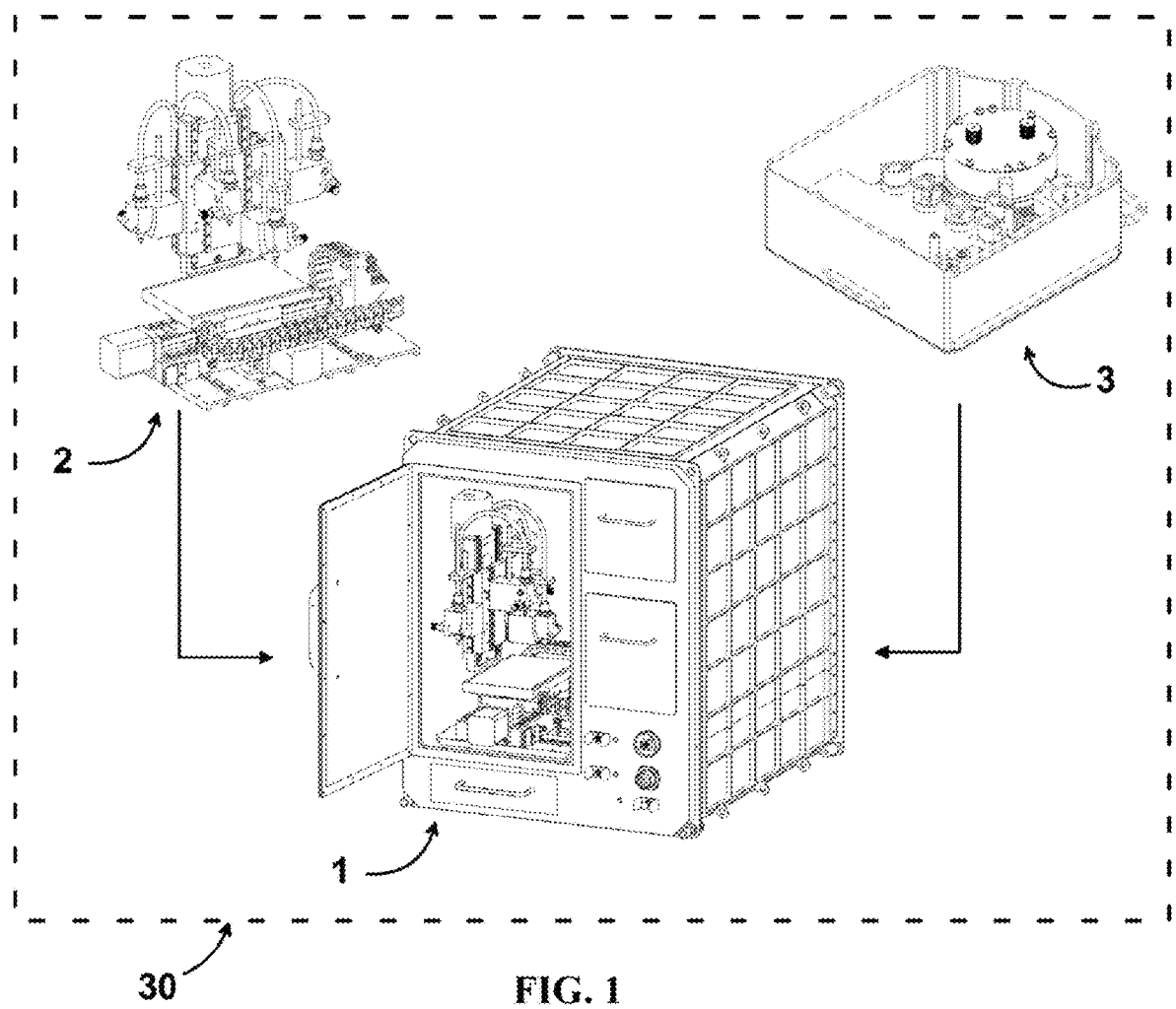
FIG. 1 illustrates an embodiment of the biomanufacturing system wherein the cell culturing bioreactor and 3D bioprinter are combined in a single integrated biomanufacturing facility capable of manufacturing tissue in reduced gravity, showing the bioprinter and the bioreactor outside the enclosure for clarity.
Figure 2:
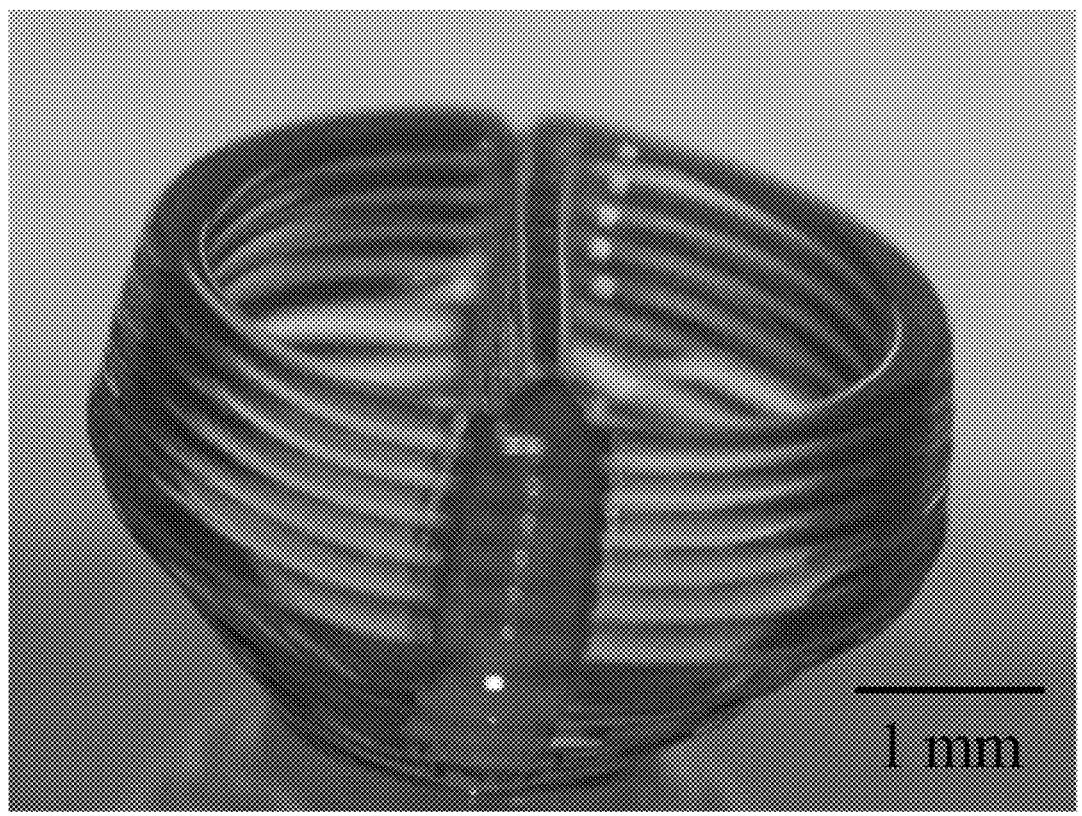
FIG. 2 is a perspective view of a prior art heart ventricle influenced by the negative effects of gravity; the material of the 3D printed structure flowed out of the desired geometry due to gravity.

Various embodiments of the invention may include a biomanufacturing system, method, and 3D bioprinting hardware optimized for exclusive use in a reduced gravity environment 30 such as that found on an orbiting spacecraft (microgravity) or another celestial body (fractional gravity). FIG. 1 illustrates a cell culturing device or bioreactor 3, a 3D bioprinter 2, and/or integrated biomanufacturing facility 1 capable of manufacturing tissue in reduced gravity. In the partial or complete absence of gravity, this system is able to construct tissues using bioinks with lower viscosities than are currently feasible for all Earth-based bioprinters. Lower viscosities allow faster printing without damaging the cells, proteins, and biomacromolecules from the effects of cavitation, high pressure, or chemical crosslinking agents. Another advantage of lower viscosity is cell motility within the printed tissue. This allows the tissues to mature faster and reduce hindrance in the formation of vascular beds used for thick tissue viability. FIG. 2 illustrates a prior art heart ventricle 4 influenced by the negative effects of gravity, resulting in deformity out of the desired shape. This deformity out of the desired pattern may result in improper function.

In addition to reduced viscosity, tissues can be built in the biomanufacturing facility 1 without or with reduced external support structures. In traditional, terrestrial additive manufacturing, overhangs may be supported either with the same material or a separate material. In either case, this material is removed after processing as it is not part of the desired tissue or end product; it is merely a means to perform bottom-up construction. In the absence of a pronounced gravitational vector, such as in the environment in Low Earth Orbit (LEO), these tissues can be built with only the functional components. This reduces the risk that supports may be forgotten and left in a tissue, or left out and have an inner passage form incompletely. Additionally, more complex geometries can be produced containing enclosed void volumes, such as the four chambers of a heart, that are unattainable using similar systems on Earth.

Finally, basic stem cell research on the International Space Station (ISS) has demonstrated improved proliferation, maturation, and differentiation. Expanding upon these findings during the culture phase of this system can produce more robust tissues and produce those tissues faster and more easily. This allows the system to use lower cell concentrations and culture for shorter periods of time than Earth-based systems to produce the same or superior tissue. For complex tissues, this time savings could be substantial. Therefore, overall both the quality and quantity of the bio tissue may be dramatically improved in reduced gravity.

The reduced gravity biomanufacturing facility 1 comprising a 3D bioprinter 2 and a cell culturing bioreactor 3, is designed to manufacture 3D living tissue in a reduced gravity environment 30 such as the microgravity environment of an orbiting spacecraft or the fractional gravity environment on the surface of other celestial bodies such as Earth's moon (1.622 meters/second/second or about one-sixth Earth's gravity) or Mars (3.711 meters/second/second or about one-third Earth's gravity). For reference, the surface of planet Earth is considered to have a unit gravity, or "1-g" environment equivalent to 9.807 meters/second/second. Microgravity is a term often used to describe the weightless conditions experienced aboard a vehicle in a state of continuous free fall as, for example, on a spacecraft in orbit around a planet. A reduced gravity environment, therefore, is any environment with a gravitational acceleration less than that of the Earth environment. The physical effects of a reduced gravity environment are a key component of successful biomanufacturing. Since the biomanufacturing equipment uses a human habitable environment (atmosphere, thermal) for living tissue, a variety of applications of, but is not limited to, microgravity spaceflight platforms may include International Space Station, commercial space stations such as the Bigelow Aerospace B330, or free-flyers such as the Space Exploration Technologies Corporation (SpaceX) DragonLab, Boeing CST-100 Starliner, or Sierra Nevada Corporation Dream Chaser®. Fractional gravity platforms might include rotating spacecraft or habitable facilities on or beneath the surface of the moon, Mars, an asteroid, or other extraterrestrial celestial bodies.

With reference to the prior art 4-layered printed wall 40 of FIGS. 8A and 8B representing printing on Earth and a similarly constructed 4-layered printed wall 50 of FIGS. 9A and 9B representing printing in reduced gravity, several advantages to reducing or removing gravity from the process are evident. Sedimentation within fluids does not occur. Under the influence of gravity, cells 41 sediment down to the 'bottom' of each printed bead 42. Even after subsequent proliferation, this initially heterogeneous distribution of cells can result in structurally weaker, less densely populated 'top' portions of each printed bead 42. Buoyance-driven stratification can also occur within the bulk material of each bead 42. Conversely, the cells 41 and bulk material of printed wall 50 are naturally homogeneous in their positions throughout. Lower viscosity fluids can be formed into 3D printed structures that still maintain their desired shapes without the complication of gravity-induced deformation. The use of lower viscosities allows faster printing without damaging the cells, proteins, and biomacromolecules from the effects of cavitation, high pressure, or chemical cross-linking agents.

Another advantage of lower viscosity is cell motility within the printed tissue and cell interaction both within a bead of printed material and across the boundary between beads of printed material. This allows the tissues to mature faster and reduces hindrance to the formation of vascular beds used for thick tissue viability. Again with reference to FIGS. 8A, 8B, 9A, and 9B, prior art FIGS. 8A and 8B show the geometry resulting from the use of high viscosity fluids to create prior art printed wall 40. Individual beads 42 virtually retain their circular cross section resulting in steep contact angles between successive beads 42 and a relatively small contact interface 43. High viscosity fluids will adhere to one another, but do not readily meld or intermix, so the area of the contact interface 43 can act as a physical barrier to both mass transport and cellular interaction between adjacent beads 42. Delamination between successive beads 42 can also occur due to the relatively small contact interface 43 and hindered ability for cells to interconnect across this interface. Conversely, and advantageously, the low viscosity beads 52 of printed structure 50 readily meld, the contact angles between adjacent beads 52 approach zero degrees as the material 'self levels' along its height due to surface tension, and contact areas 53 between adjacent beads 52 all but disappear. The resulting printed structure 50 has a much more uniform overall width, cell and extracellular material distribution, and integrity.

In a reduced gravity environment, 3D bioprinter 2 can print using low viscosity extrudable materials, hereafter referred to as bioinks, that may have one or more of the following components: natural and synthetic structural proteins, such as fibrinogen, albumin, fibronectin, collagen, or hyaluronic acid; polymers, such as pluronic or urethanes; living biological components, such as undifferentiated stem cells, partially differentiated stem cells, terminally differentiated cells, microvascular fragments, or organelles; macromolecules; or pharmaceuticals. These bioinks may have a viscosity as low as approximately 1 centipoise on the low side, and have viscosities on the high side of typical bioinks used in terrestrial applications (for example, on the order of 10,000,000 centipoise). Preferably the range of viscosity is approximately 5 to 2,000 centipoise. On Earth, under the influence of gravity, structures printed using such low viscosity bioinks cannot maintain their initial shape and will deform or structurally fail under their own weight. Internal and/or external scaffolds of like or dissimilar materials may be constructed to maintain the initial shape. These scaffolds are subsequently removed. However, in a reduced gravity or near-weightless environment, complex shapes such as cantilevered overhangs and enclosed voids, such as the enclosed chambers of a heart, can be easily maintained. Yet another advantage of printing in a reduced gravity environment is the ability to build up cantilevered overhangs that simply cannot be made on Earth, even with supporting scaffolds. On Earth, each new extruded bead typically contacts 75% or more along the length of the bead directly beneath it. Therefore it utilizes many stacked but only slightly offset layers to incrementally build a cantilevered structure. In a reduced gravity environment, the goal is to create structures wherein less than 50% of a new extruded bead makes contact along the length of the bead directly beneath it. This will enable thinner overall printed structures and steeply cantilevered geometries that simply cannot be made on Earth using any conventional means.

FIG. 2 demonstrates the root cause of further benefits of printing in reduced gravity using low-viscosity bioinks. In the additive manufacturing process of bioprinting, material is extruded in successive layers. The high viscosity bioinks used to terrestrially print the ventricle 4 shown in FIG. 2 maintain clearly distinct layers on the final structure. The boundaries between successive layers act as both physical and chemical barriers to cell proliferation. Cells can relatively easily interact within a single layer, but not across layer boundaries. The use of low viscosity bioinks advantageously results in little or no clearly defined layers in the resulting 3D printed structure, thereby promoting and accelerating the interaction between cells in different layers and leading to a more robust final product.

Figure 3:
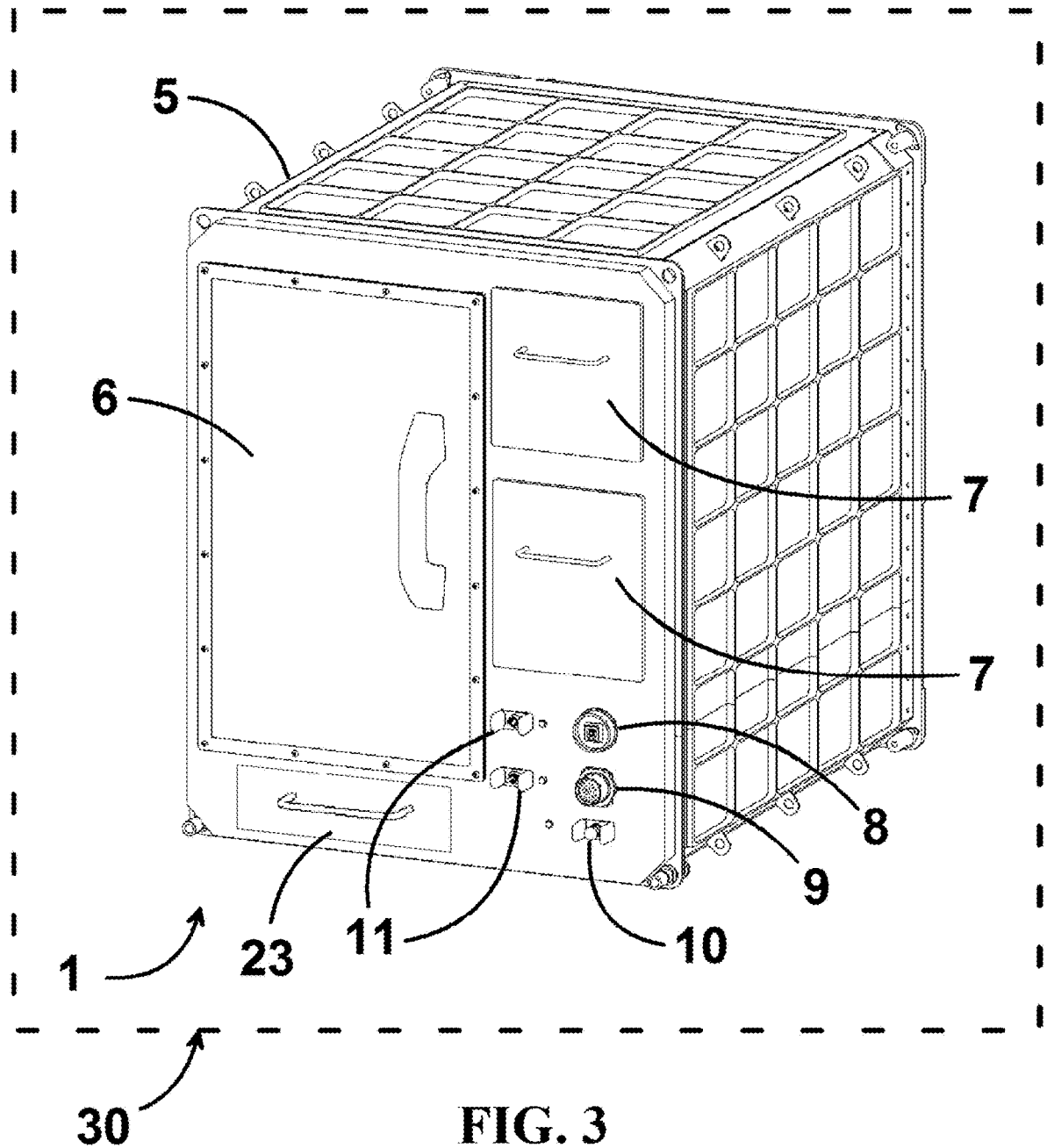
FIG. 3 is a perspective view of the integrated reduced gravity biomanufacturing facility of FIG. 1 with the door closed.
Figure 4:
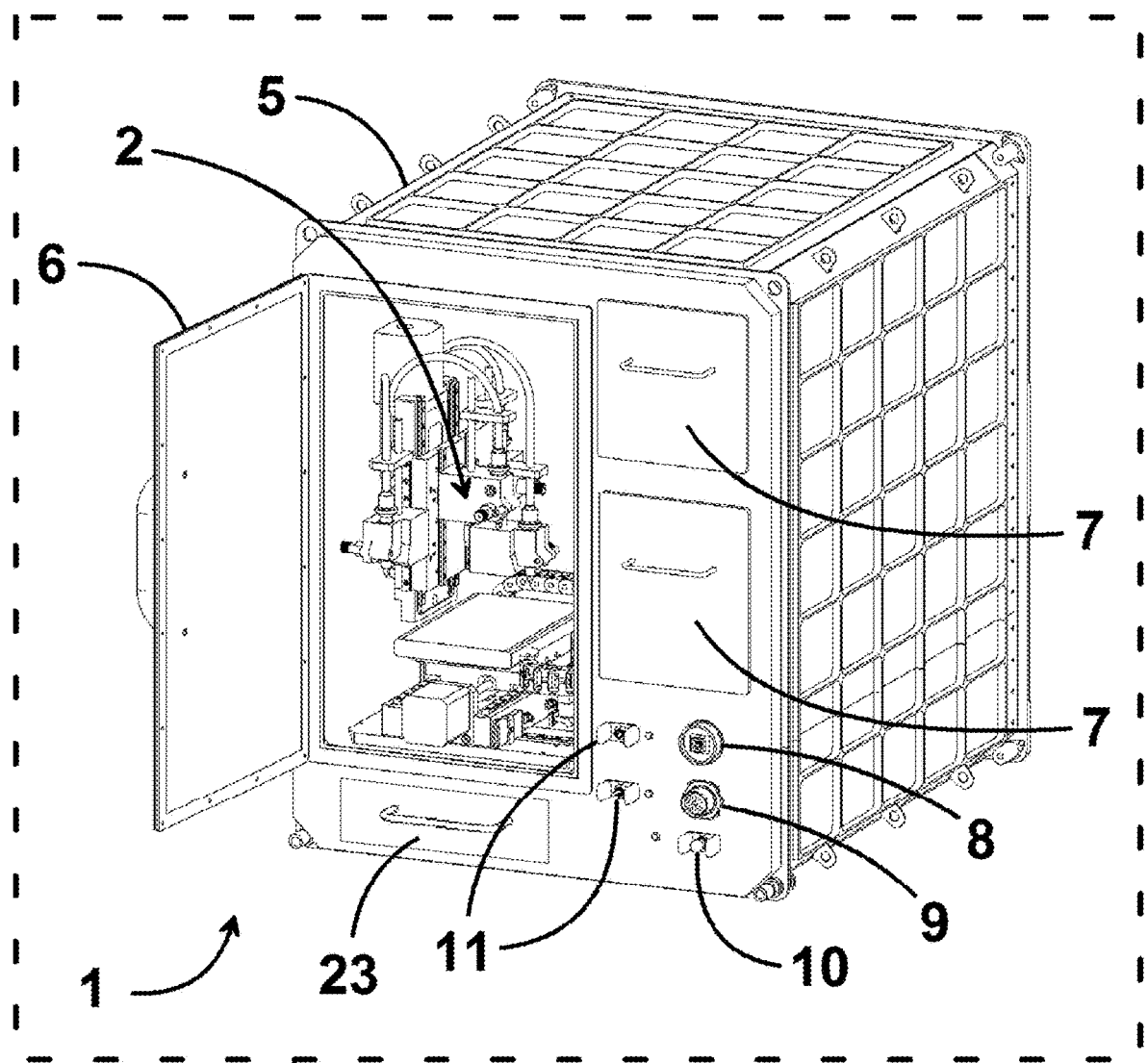
FIG. 4 is a perspective view depicting the general layout of some of the exterior biomanufacturing facility components with the door open.

The reduced gravity biomanufacturing system comprises, at a minimum, two major subsystems: a 3D bioprinter and a cell culturing bioreactor in which a printed structure is incubated to promote cell proliferation, differentiation, and remodeling into a final product tissue. In one embodiment, both subsystems occupy discrete and separate facilities. Precautions may be taken to prevent physical damage or exposure to deleterious environmental microorganisms during transfer between subsystems. In a preferred embodiment, both subsystems are contained within a single integrated facility. This embodiment reduces or eliminates moving a structure from bioprinter to bioreactor and protects the biomaterial during all stages of processing. FIGS. 3 and 4 show an embodiment of the reduced gravity biomanufacturing system whereby both 3D bioprinter 2 and bioreactor 3 are housed in one integrated biomanufacturing facility 1. Biomanufacturing facility 1 is a modular box-like volume with an overall geometry compatible with the generic interface requirements for various spacecraft or habitable systems. External enclosure or housing 5 includes a door 6 for operator access to the environmentally controlled interior chamber where 3D bioprinter 2 and cell culturing bioreactor 3 (not shown) reside. External enclosure 5 surrounds and supports the individual assemblies and components within the unit and has exterior dimensions, in the embodiments shown, that are approximately 21 inches×21 inches×18 inches (essentially a spaceflight double locker typical of the art). Several notional switches 11 enable overall power to major subsystems. Circuit breaker 10 provides facility overcurrent protection consistent with the requirements levied by the habitable platform. Power connector 9 and data connector 8 are typical multi-pin shrouded connectors typical in the art for providing electrical interfaces to a vehicle or facility. Consumables bays 7 house stock materials that are consumed by the 3D bioprinter 2 or cell culturing bioreactor 3 major subsystems. Consumables may include one or more of bioinks used to print 3D structures, media to perfuse a 3D printed structure during cell proliferation, thermoplastic feed stock that can be used to manufacture in situ bioreactor enclosures, and compressed gas supplies such as oxygen used to maintain culturing cells. The hardware is designed in a modular configuration so that both major systems and some individual components can easily be swapped-out on orbit for resupply, refurbishment, or upgrade as technology advances. Modularity is further facilitated by design features such as the use of captive fasteners that cannot be lost during removal in reduced gravity; self-aligning blind-mate electrical and mechanical connectors between modular subsystems; logical grouping of low mean time between failure (MTBF) and high MTBF components separately to minimize the mass and volume of replacements; grouping of certain electrical components within electromagnetic interference shielding; and colocation of elements requiring air or liquid cooling such as power supplies, thermoelectric Peltier devices.

A computerized command and data management system (CDMS)/power supply 23 provides power, monitors, and controls operation of the facility 1. The electrical system components and topology are typical of those in the art of manufacturing high reliability, high safety equipment for the medical, defense, or aerospace fields. For example, the present invention uses a federated control architecture to reduce the risk of major system failure resulting from the radiation and high-energy particles often encountered in reduced gravity environments such as space. (CDMS)/power supply 23 conditions the power and provides the voltage levels used by the biomanufacturing facility as well as providing electromagnetic interference filtering and electrical bonding. Software employed internally to operate and control components such as pumps, sensors, motors, and data acquisition are typical for computer controlled electromechanical systems. Facility 1 has the ability to monitor and control all of the system parameters real time with the added flexibility of being able to uplink and downlink files, video, and operating data at any time. The facility uses software and physical interfaces to various host vehicles or platforms that are compatible with command and control interfaces typical in the art such as universal serial bus (USB) and Ethernet. It may incorporate a digital display with a user-friendly graphical user interface (GUI). CDMS/power supply 23 may be housed within enclosure 5 or may be a separate entity (not shown) connected via cables (not shown) to respective data connector 8 and power connector 9. In a general sense, tasks performed by the biomanufacturing system may be performed manually by an operator, semi-autonomously, or fully autonomously with or without remote monitoring. For example, the remote monitoring may be at least partially from a terrestrial location. Biomanufacturing facility 1 may be ergonomically designed to facilitate ease of use by an operator in a reduced gravity environment.

Figure 5:
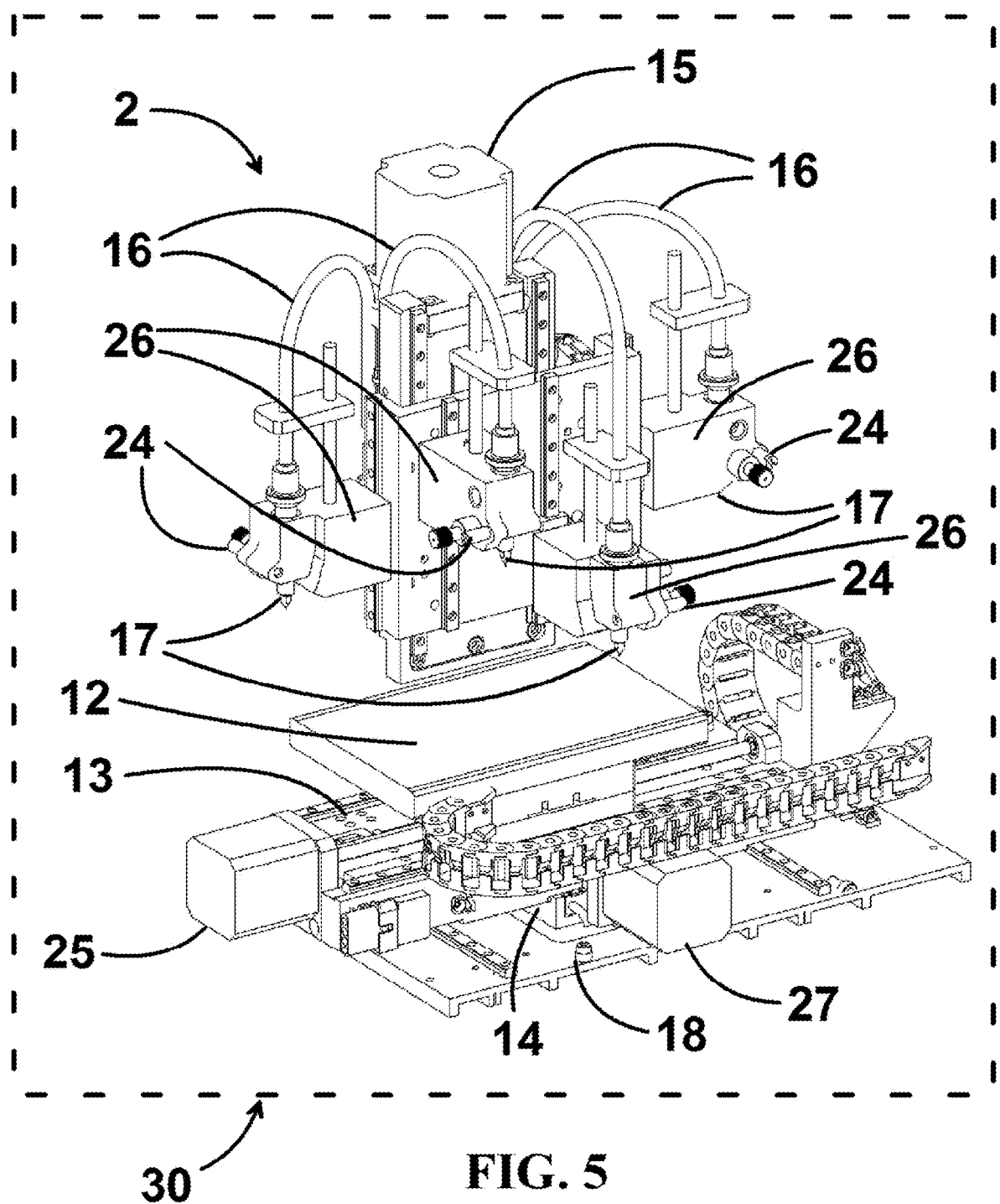
FIG. 5 is a perspective view of the reduced gravity 3D bioprinter print stage and interdependent systems that translate the stage and feed the bioinks to the print heads.

FIG. 5 describes the reduced gravity 3D bioprinter 2 in greater detail. One or more print stages 12 comprises a flat plate that can be thermally controlled as desired. This plate may be metallic or nonmetallic, surface treated or untreated, removable or non-removable. In a preferred embodiment, print stage 12 is mounted to x-axis support structure 13 and y-axis support structure 14. Print stage 12 translates in two axes utilizing X-motion control system 25 and Y-motion control system 27 to move in the X-direction and Y-direction respectively. In the preferred embodiment, control systems 25 and 27 comprise computer controlled brushless DC servo motors common in the art to control the accuracy, repeatability, resolution, and velocity of print stage 12 during the bioprinting process. Support structures 13 and 14 are mounted within enclosure 5 via vibration isolators 18 to further facilitate precision in the printing process. Z-axis support structure 15 is mounted on an interior sidewall of enclosure 5 directly above print stage 12. Each print head 17 includes an associated visualization system 24 and dispensing system 16 that will be described hereafter in greater detail. In a preferred embodiment, one or more print heads 17 each include individual Z-motion control systems 26 capable of independently translating print heads 17 in a third, or Z-axis that is substantially orthogonal to the x-y plane defined by print stage 12. For example, control system 26 may comprise one or more computer controlled brushless DC servo motors to control the accuracy, repeatability, resolution, and velocity of one or more print heads 17 during the bioprinting process. In an enhanced embodiment, additional means for Z-axis translation of dispensing system 16, and all print heads 17 may be desirable to facilitate post-printing access to print stage 12. Using one or more translation or motion control systems such as but not limited to 25, 26, and 27, the relative position of print stage 12 and interdependent systems can translate in the x-, y-, and z-directions up to about 12 inches and feed stock to the print heads in the embodiment shown. In a second embodiment, print stage 12 and, optionally, visualization system 24, may translate in the z-direction while print heads 17 and dispensing system 16 may translate in the x- and y-directions. In a third alternate embodiment, print stage 12 may remain in a fixed location while z-axis support structure 15 and dependent elements may translate in the x-, y-, and z-directions. In a fourth alternate embodiment, z-axis support structure 15 and dependent elements remain fixed while print stage 12 may translate in the x-, y-, and z-directions. Each of the three alternate embodiments utilize different associations with motion control systems 25, 26, and 27 than shown in the preferred embodiment of FIG. 5. While weightless, or nearly weightless, the printed structure still experiences momentum. Abrupt changes in direction of the printed structure may result in deformity. In some combinations of translation interdependency described above, the printed structure remains stationary or moves minimally in the x-direction, particularly those wherein print heads 17 translate in the x- and y-directions. In combinations wherein print stage 12, and hence the printed structure, translate in the x- and y-directions, both translation acceleration and velocity are carefully controlled to mitigate momentum effects.

Working in concert with print stage 12 is multi-solution dispensing system 16 that incorporates precision control of the feed rates of the bioink fluids delivered to one or more removable and replaceable print heads 17. Being a dynamic system capable of 6-axes of freedom, dispensing system 16 is also able to maintain dynamic flow control during the bioprinting process all within a thermally controlled environment. Dispensing system 16 also provides precise start and endpoint volumetric control. Print technologies comprise two groups: point by point "ink jet" printer-based, also called laserjet printing, or point and line "direct write"

syringe-based. In a direct write system, pressure is maintained, either mechanically (linear motor, drive screw) or pneumatically (vacuum, pressurized gas, pressurized drive fluid), on a reservoir of bioink that is ejected through a small gauge needle or extruder tip to the printing substrate which is often temperature controlled. Feed is enabled by control of a valve (not shown). The feed rate and the ability to start and stop the flow of material differentiate the systems as well as the ability to handle a wide range of working fluid viscosities. The preferred embodiment utilizes direct write print heads such as the SmartPump™ manufactured by nScrypt, Inc. (Orlando, Fla.) and may use either a very fine needle or a very fine ceramic tip extruder. The diameter of the extruded material is typically in the range of 12.5 to 125 micrometers. A plurality of print heads can be simultaneously or serially orchestrated to incorporate several different bio-inks into the printed structure. This feature may allow the production of complex structures such as organs that may utilize several different functional tissue types. As described below, some print heads may print non-biological material such as thermoplastics to build in situ bioreactor vessels or electrically conductive material to electrically connect prefabricated sensors that can be incorporated into the 3D printed tissue. Surfaces of print heads 17 and/or print stage 12 may be natively, or treated to be, hydrophobic or hydrophilic in order to urge the proper behavior of the extruded bioinks. Physical forces such as surface tension are known to play a more dominant role in reduced gravity fluid dynamics.

Illuminated visualization system 24 may have one or more small cameras, associated with each print head 17, focused on print stage 12 plus either visible or infrared illumination as is typical in the art such as LED lighting. Visualization system 24 may incorporate the ability to capture both still and video images of the entire bioprinting process. The frame rate, resolution, and field of view are all fully programmable. Illumination can be turned on or off by an operator as desired. Observation of the structure during printing enables an operator, one who may be observing directly or via remote telemetry, to make real time corrections as the print develops.

A quiescent, biologically compatible environment may be provided during one or more steps of the biomanufacturing process. One or more components of the biomanufacturing facility 1 can control both the temperature and humidity environment. Typical spacecraft ambient environments are in the temperature range of 20-25° C. with a low relative humidity in the range of 30-50%. The enclosable internal volume of biomanufacturing facility 1 surrounding 3D bioprinter 2 can be maintained and controlled at approximately the same ambient temperature in the range of 20-25° C., but relative humidity may be controlled at an elevated but noncondensing 70-90% in order to mitigate desiccation of the printed structure while it is being processed. Atmospheric control systems used to heat, cool, humidify, and dehumidify enclosed volumes in a habitable reduced gravity environment are well known in the art of closed environmental life support systems used in spacecraft design. Some components of 3D bioprinter 2, specifically, print stage 12 and print heads 17, may have active thermal control independent of the bulk internal volume environment to enhance the quality and integrity of the biomaterial being printed. If desired to be used, certain chemical or biochemical reactions of the bioinks utilize heating or cooling relative to the ambient environment of the 3D bioprinter at the time of extrusion or incorporation into the printed structure. The bioreactor encloses the 3D printed structure and bathes it in liquid media thermally controlled to maintain the body temperature of the organism compatible with the printed tissue. Typically, this will be human body temperature of approximately 37° C. The facility is designed with vibration isolation for the print stage to insure the material is printed with high precision.

After the tissue is printed, whether in the present bioprinter 2 or another, these neo-tissues need to mature before they gain the strength and function to be transplantable. This maturation will be accomplished in a bioreactor 3 that utilizes a feedback control system to supply the growing tissue with oxygen and nutrient medium (glucose, trace elements, etc.), remove waste metabolic products and carbon dioxide, maintain optimal pH, minimize the accumulation of air bubbles, and facilitate cell proliferation, differentiation, and tissue remodeling. The design of compatible bioreactors is well known in the art including bioreactors designed for use in low gravity (such as in U.S. Pat. No. 7,198,940 incorporated herein by reference). Typically they include means (not shown) for a liquid media supply reservoir, a liquid waste reservoir, pumps for circulating media, heating and cooling, oxygenation, degasification, sensors, and monitored feedback control systems.

In one embodiment, the printed structure may be physically removed from print stage 12 and transferred into a separate cell culturing bioreactor 3 by an operator or robot. In this embodiment, bioreactor 3 may be collocated along with bioprinter 2 within biomanufacturing facility 1. Alternatively, bioreactor 3 may be in a different location not associated with biomanufacturing facility 1. A removable bioreactor 3 may be packaged to include its own integrated life support systems so that it can serve a second function of maintaining the printed and cultured tissue in fluid living homeostasis for transportation and return to a patient on Earth or an alternate, extraterrestrial destination. Such a 'transportation compatible bioreactor' would include adequate robustness of design to survive the vibration environment experienced during planetary descent and possible refrigeration necessary to extend longevity of the printed and cultured tissue. In an alternate embodiment, a removable bioreactor 3 may be designed to interface with a host transportation carrier capable of providing power and life support to at least one bioreactor during transportation and return.

In a second embodiment, the print stage itself may be transformed into a cell culture type vessel that becomes bioreactor 3. This may be accomplished by simultaneously or serially printing both a bioink and a thermoplastic using two print heads to create both the biological structure and its enclosing culture vessel.

In a third embodiment, bioreactor 3 may comprise an open-topped prefabricated and pre-plumbed enclosure 20 mounted on print stage 12. This third embodiment allows print head 17 the requisite access to print stage 12 to dispense the bioinks within pre-plumbed enclosure 20. Once the bioprinted structure is completed, either a prefabricated lid may be installed and sealed on enclosure 20 to create bioreactor 3 or, alternatively, a second print head 17 could extrude thermoplastic to print a lid or top fastener directly on prefabricated enclosure 20.

Any of these embodiments may be enhanced by bioreactor 3 providing any of equibiaxial mechanical loading in tension, electrical stimulation, fluid shear, or compression. Mechanical loading in tension may be provided by printing the tissue construct on a flexible membrane. On the opposite side of the flexible membrane, a pressure or vacuum source may be attached causing the membrane to distend and impart tension into the tissue. This stretching is known to induce maturation in many cell types including cardiomyocytes. The bioreactor may include means to both induce and monitor electrical stimulation for depolarization currents in cardiac tissues. The ability to capture the spontaneous contraction of cardiomyocytes and pace a tissue is another indication of maturation. Terrestrial bioreactors providing mechanical loading, electrical stimulation, fluid shear, or compression are known in the art.

One embodiment of the reduced gravity biomanufacturing system having the previously described hardware can have at least one suite of software tools to create, edit, import, model, simulate, and control the biomanufacturing system to produce the tissue and the supporting structures or components for the creation, culture, transfer, or implantation of the printed tissue. The system can import and modify image files from medical imaging formats to create geometries defining tissues or organs to be printed. The imaging technology can be selected from magnetic resonance imaging, computerized tomography, X-ray radiography, medical ultrasound, endoscopy, tactile imaging, medical photography, positron emission tomography, and nuclear magnetic resonance imaging. The system may output an electronic model file used by another software or hardware platform to visualize the tissue before 3D printing. The biomanufacturing system software tools can modify the tissue model in either two-dimensional sketching or three-dimensional modeling environments to correct, clarify, add, modify, remove or generally change the imported or originally produced geometry. The method can be done with bound or unbound constraints and can be driven by individual changes, a lookup table or a mathematical equation bound by user defined variables.

Figure 6:
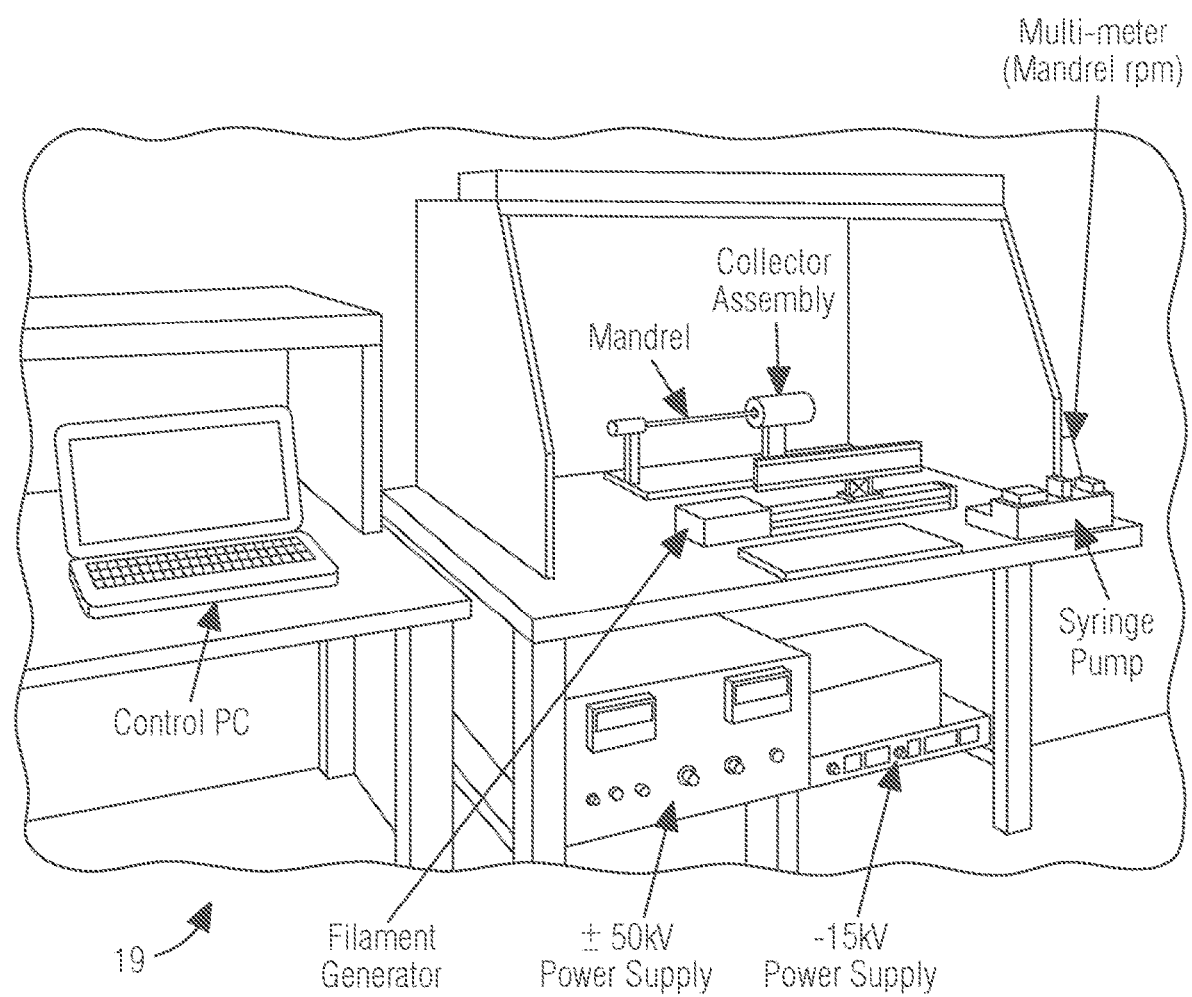
FIG. 6 is a perspective view of prior art terrestrial electrospinning hardware used to make prefabricated structures that can be incorporated into bioprinted tissues.
Figure 7:
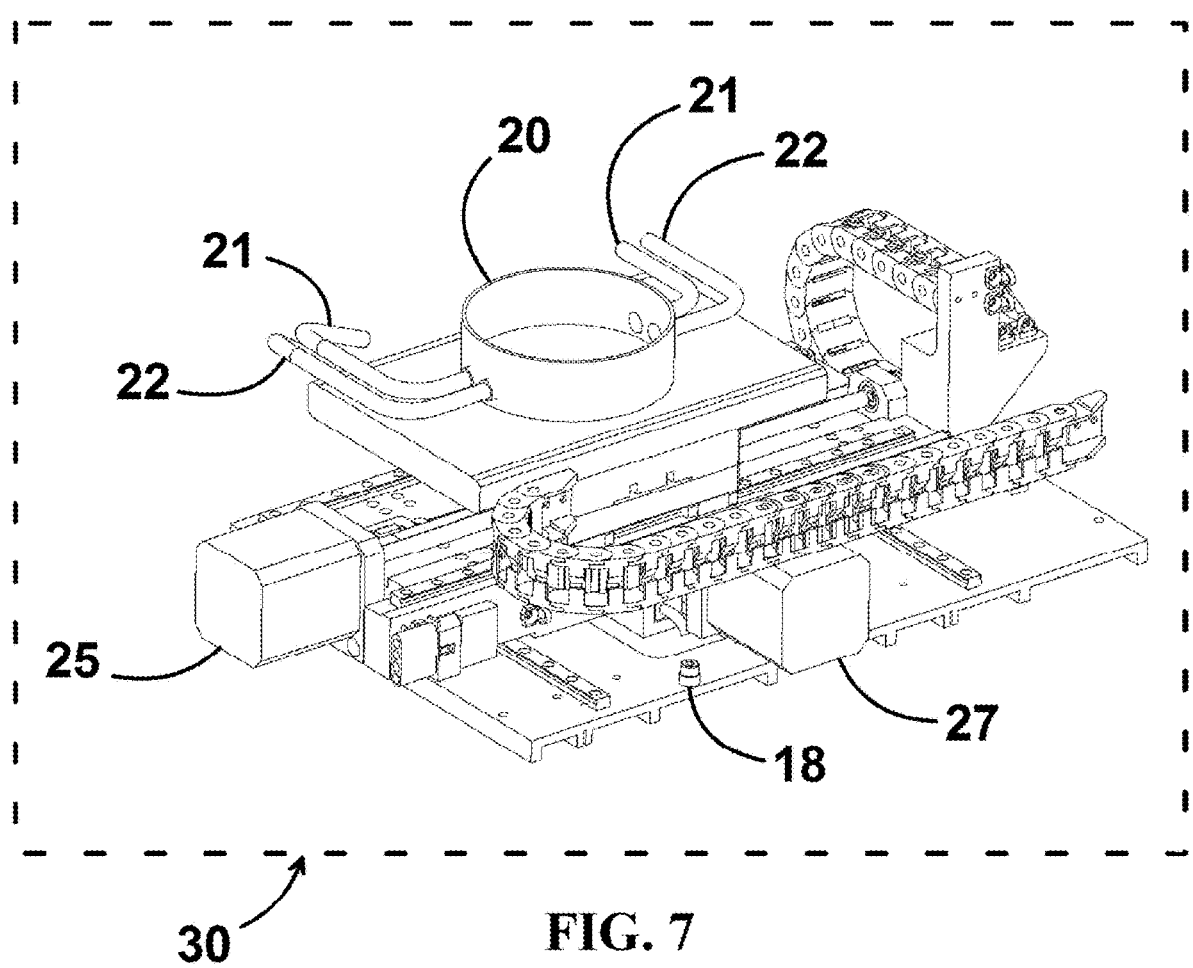
FIG. 7 is a perspective view of an embodiment of the print stage including a flexible bioreactor capable of mechanical and electrical stimulation of a printed tissue.

Some biomanufactured tissues or organs may include prefabricated structures such as large blood vessels that are incorporated before, during, or after 3D bioprinting in reduced gravity. Prefabricated structure of the tissue or organ can be created by at least one of electrospinning, electrospraying, electroaerosoling, or electrosputtering and can have three-dimensional scaffolds within or upon the bioprinted tissue or organ (See FIG. 6 prior art electrospinning hardware). This method can be used for at least one of the creation of the tissue or organ, support structure, perfusion aid, implantation aid, cell delivery, or reagent delivery. Additionally, prefabricated sensors can be incorporated into the 3D printed biomaterial or printed in place using electrically conductive biocompatible feed stock. These incorporated sensors may have the ability to provide data during the maturation process or following implantation in a target organism such as a human patient.

The reduced gravity biomanufacturing system may include a material dispensing system capable of printing bioinks. One method of manufacturing includes wherein part or all of the tissue may be created using a print head utilizing a direct-write printing approach driven by mechanical plunger driven by vacuum, pressurized gas, pressurized fluid, linear motor, or drive screw to express the bioink. The dispenser tips for the print head can have a single or multiple bores to express one or more bioinks simultaneously. The dispenser tips can be driven by a single or multiple print heads. The system can contain one single material or multiple materials. The method wherein part or all of the structure of the tissue or organ can be created by at least one of electrospinning, electrospraying, electroaerosoling, or electrosputtering. The methods can incorporate three-dimensional scaffolds within or upon the bioprinted tissue or organ. The methods can be used for at least one of the creation of the tissue or organ, support structure, perfusion aid, implantation aid, cell delivery, or reagent delivery. The reduced gravity biomanufacturing system may print an accurate, biologically viable reproduction of the desired tissue or organ and can transfer the printed tissue or organ into a perfused bioreactor chamber upon completion of printing automatically. Alternatively, the transfer may be done manually. The process can be performed robotically with reduced damage or contamination of the tissue or organ printed. The reduced gravity biomanufacturing system may culture the printed tissue or organ automatically to mature the tissue. The system may provide a method to perfuse the tissue and the developing vascular network. The system may allow the tissue to be removed from the reduced gravity biomanufacturing system and returned to Earth while remaining viable and suitable for transplant. The reduced gravity biomanufacturing system can be cleaned in place and reset with expendable bioreactor chamber, print head cartridges, dispenser tips, media, bioinks and image file by an astronaut and verified remotely.

Bioreactor

In some implementations as shown in FIGS. 10-17, the one or more bioreactors 300 may be constructed for receiving one or more tissues 150 (e.g. same or different tissues) corresponding to the requirements needed to print and/or culture the desired tissue. The bioreactor 300 may be used to condition or culture a number of tissues 150, including skeletal muscle, bone, cartilage, neuronal, kidney, liver, etc. In some embodiments, the bioreactor 300 may include an ADSEP (Advanced Separation by Phase Partitioning) cassette, or a MVP (Multipurpose Variable-g Platform) cassette permitting culturing constructs in variable gravity environments (e.g. microgravity to 2 g). The bioreactor may provide post-print conditioning of the 3D bioprinted constructs and tissues 150 by construct perfusion and/or imparting cues to drive differentiation of the construct. The bioreactor 300 may be used to provide at least one of perfusion, electrical stimulation, and/or mechanical stimulation to the construct 150. Once the construct dimensions pass the diffusion distance of gasses, ions, metabolites, and proteins, an internal network of printed blood vessels (e.g. vessel-like structures) may deliver these entities to the internal cells of the 3D printed construct. With perfusion established in the bioreactor, the cells may be given cues to drive them to differentiate. For example, in applications where the printed tissue is cardiac tissue, a variety of mechanical and/or electrical stimulations may provide a conditioning environment similar to signals within or from a heart.

In some implementations, the bioreactor 300 may include a housing 310 for conditioning the printed construct 150. The housing 310 may define a volume 311 therein. The housing 310 may include a lid 312 and base 313 positionable between an open position (see FIG. 10) and a closed position (see FIGS. 11 and 12). When in the open position, the tissue may be printed into the base 313 and/or on one or more print platforms 314. Alternatively, the printed tissue 150 may be transferred to the housing 310 in some embodiments. When in the closed position, the lid 312 may be sealed with the base 313. For example, one or more O-rings or seals (not shown) may be used between the lid 312 and base 313 to create a sealed volume 311 therein. In some embodiments, a portion of the housing 310 (e.g. lid) may be translucent or transparent allowing visual conditions of the printed tissue to be observed while conditioning. For example, the bioreactor 300 may include a camera, video system, sensors, or monitoring device 301 to visually observe or other monitoring systems to track conditioning. Monitoring the conditions or characteristics of the tissue (e.g. visual) may allow for adjustments (e.g. manual and/or automatic) of one or more materials/media via the perfusions, electrical stimulation, mechanical stimulations, and/or other cues during the conditioning.

Figure 10:
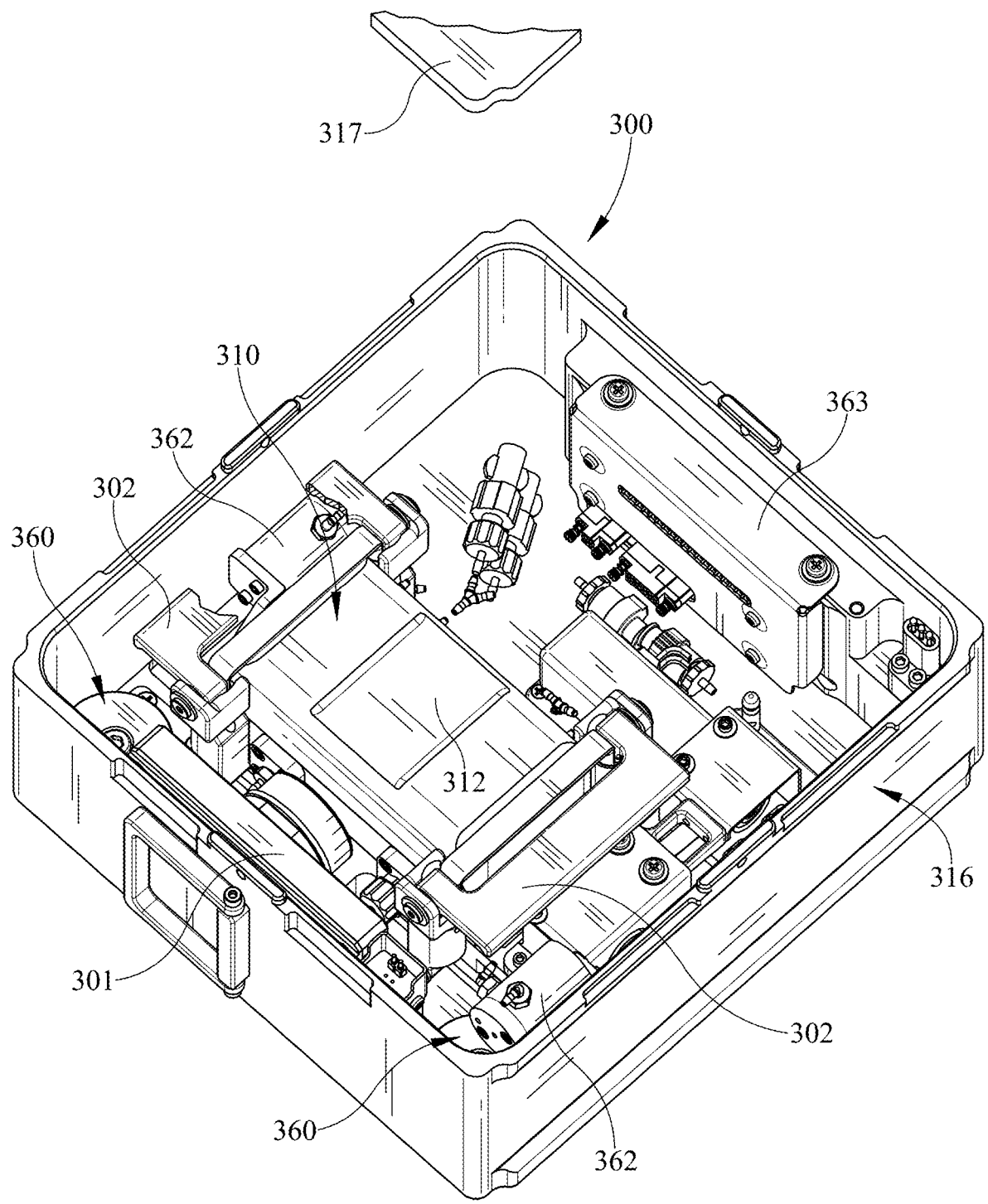
FIG. 10 is a perspective view of another embodiment of a bioreactor with the cassette lid exploded therefrom.

In some embodiments, the housing 310 may include a locking mechanism 302 to secure the lid 312 in the closed and/or sealed position with the base 313. As shown in FIG. 10, the one embodiment of the locking mechanism 302 is one or more clamps or fasteners sealing and/or locking the lid 312 with the base 313. Locking the lid may also compress the one or more seals/gaskets creating the seal for the internal volume 311.

In some implementations, the bioreactor may provide one or more perfusions to the printed construct 150. As shown in the figures, the bioreactor 300 may include one or more perfusion ports 331 adapted to be in fluid communication with the 3D printed construct 150. The perfusion ports 331 may be in fluid communication with the printed tissue 150 in one directional flow (see FIG. 17) as shown in the one embodiment, however the fluid flow may be in more than one direction. The one or more fluid flows through the one or more ports 331 may be a variety of flow rates (e.g. variable or constant). For example, one or more ports 331 may have the same or different flow rates. Moreover, the flow rates may change or be different within a single port or array of ports. The one or more ports 331 (e.g. outlet ports) may also be positioned in downstream fluid communication with the 3D printed construct 150 and the upstream ports 331 (e.g. intake ports) may be positioned upstream of the construct 150. The one or more ports 331 (e.g. intake and/or outlet ports) may be a variety of quantities, positions, constructions, shapes, and sizes and still be in communication with the 3D printed tissues (e.g. vessel structure).

In some implementations, the bioreactor 300 may include one or more manifolds or members 330 engaging the constructs 150. The one or more manifolds 330 may be in fluid communication or perfusion with the 3D printed construct 150. One or more intake manifolds 330a may include one or more ports 331 (e.g. intake ports). One or more outlet manifolds 330b may include one or more ports 331 (e.g. outlet ports). The intake manifold 330a and outlet manifold 330b (e.g. ports) may be in fluid communication with the 3D printed construct. In some embodiments, the intake manifold 330a may include a plurality of channels 332 in communication with one or more of the ports 331 therein. The channels 332 may provide for substantially the same flow rate or material to pass through the one or more ports 331 of the intake manifold 330a. The one of more channels 332 or ports 331 of the intake manifold 330a may be supplied by at least one supply conduit 333. As shown in the one embodiment in FIGS. 15 and 16, the outlet manifold 330b may include downstream engagement with the construct 150 (e.g. vessel structures). The ports 331 of the outlet manifold 330b may be in communication with the volume 311 of the housing 310 via an interconnecting chamber 334 within the outlet manifold 330b. If a chamber 334 is used, the chamber may be recessed within the outer periphery of the manifold.

In some embodiments as shown more clearly in FIGS. 13-16, the one or more ports 331 may be defined by one or more needles 335 in one or more of the manifolds. As shown in the figures, both the intake and the outlet manifolds 330a, 330b have ports 331 defined by needles 335 projecting inwardly towards the printed construct 150, print platform 314, and/or other manifold 330. The ports 331 and/or needles 335 may be inserted into structure of the 3D printed construct 150. The ports 331 and/or needles 335 may be a variety of shapes, sizes, quantities, constructions, and/or have a variety of through openings therein. For example, the ports 331 may have uniform/non-uniform inner diameters.

Figure 11:
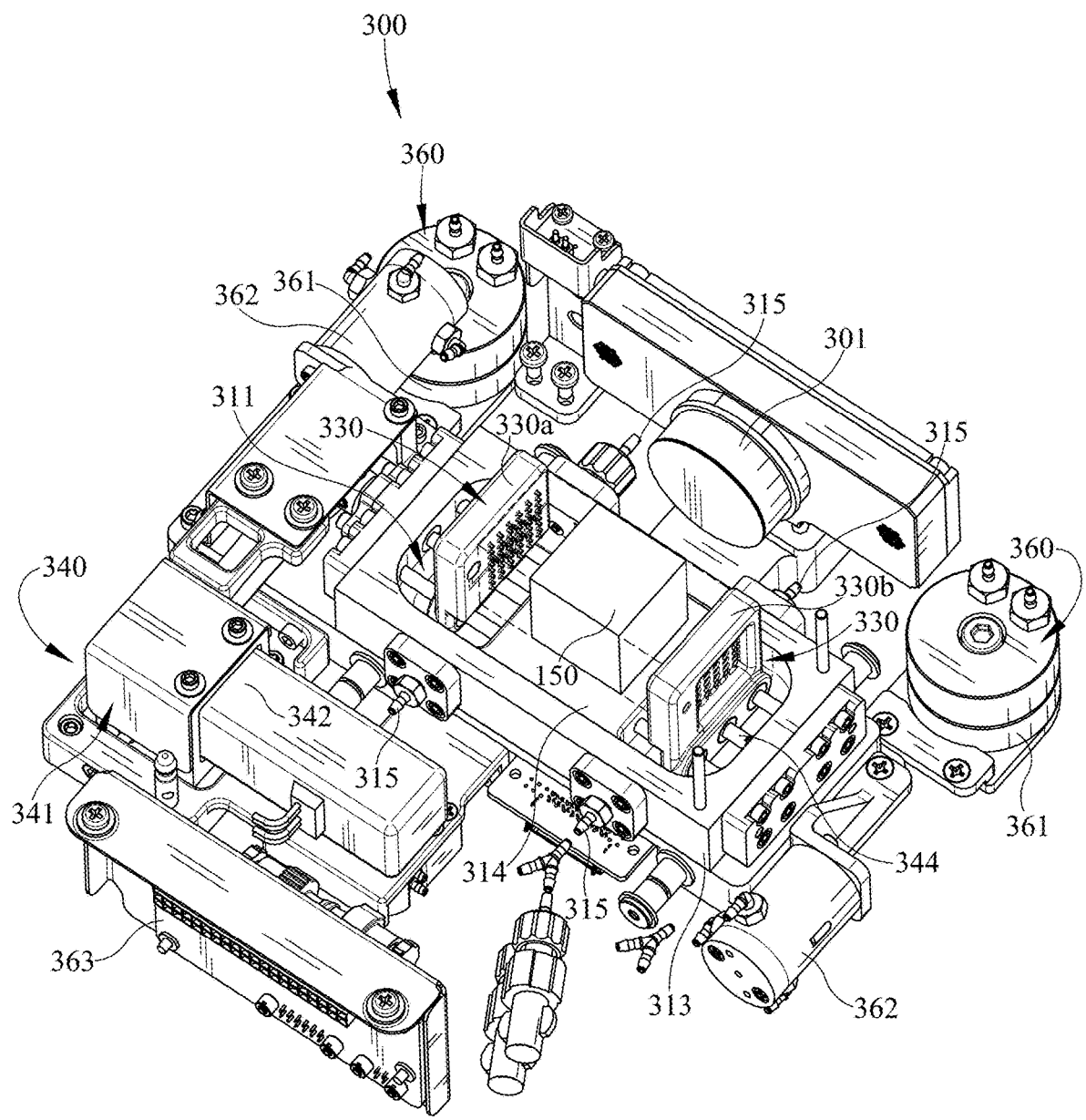
FIG. 11 is a perspective view of the bioreactor of FIG. 10 rotated 180 degrees with the cassette, locking mechanism, housing lid removed illustrating an embodiment of the manifolds disengaged from the bioprinted construct.
Figure 12:
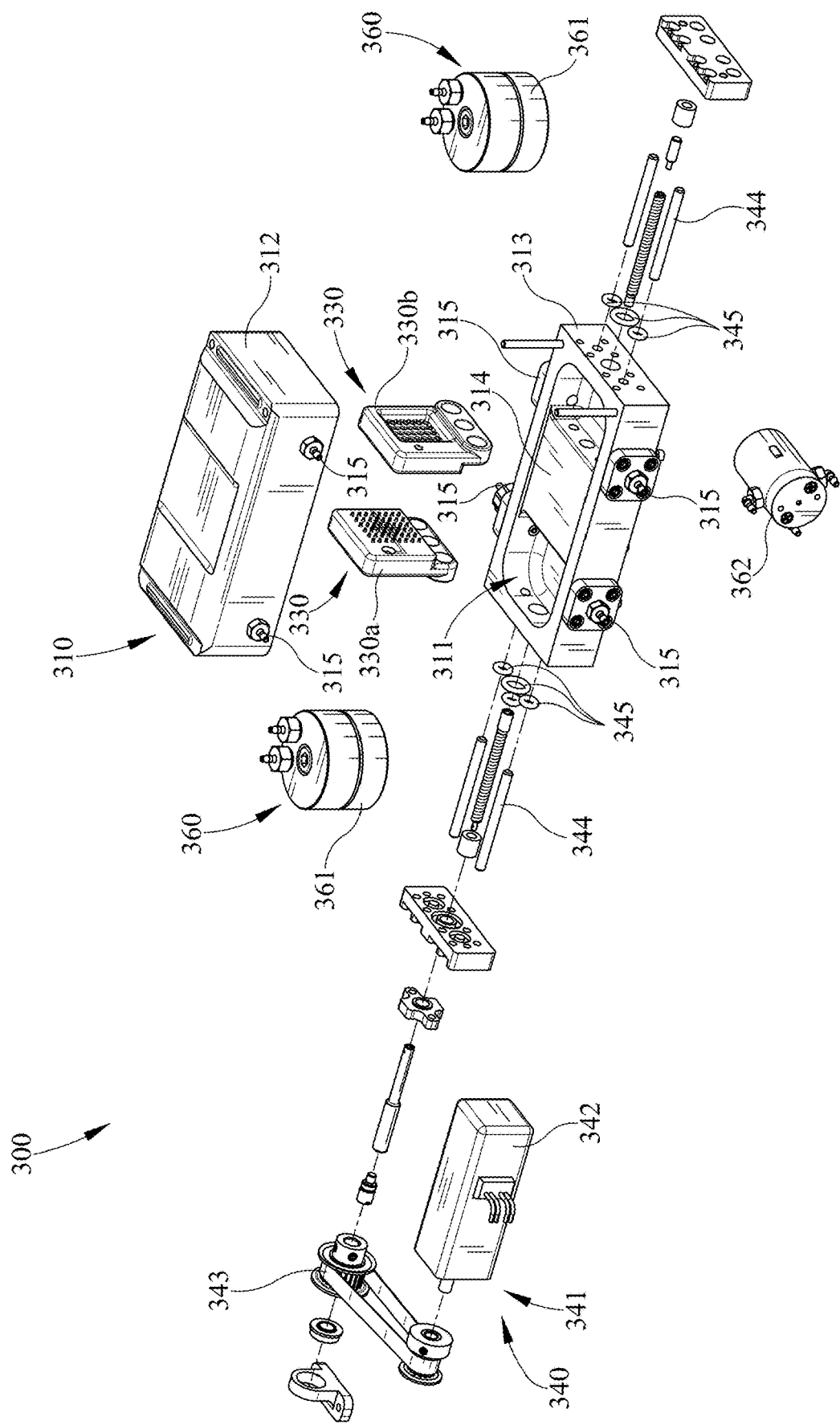
FIG. 12 is a perspective exploded view of the bioreactor of FIG. 10.
Figure 15:
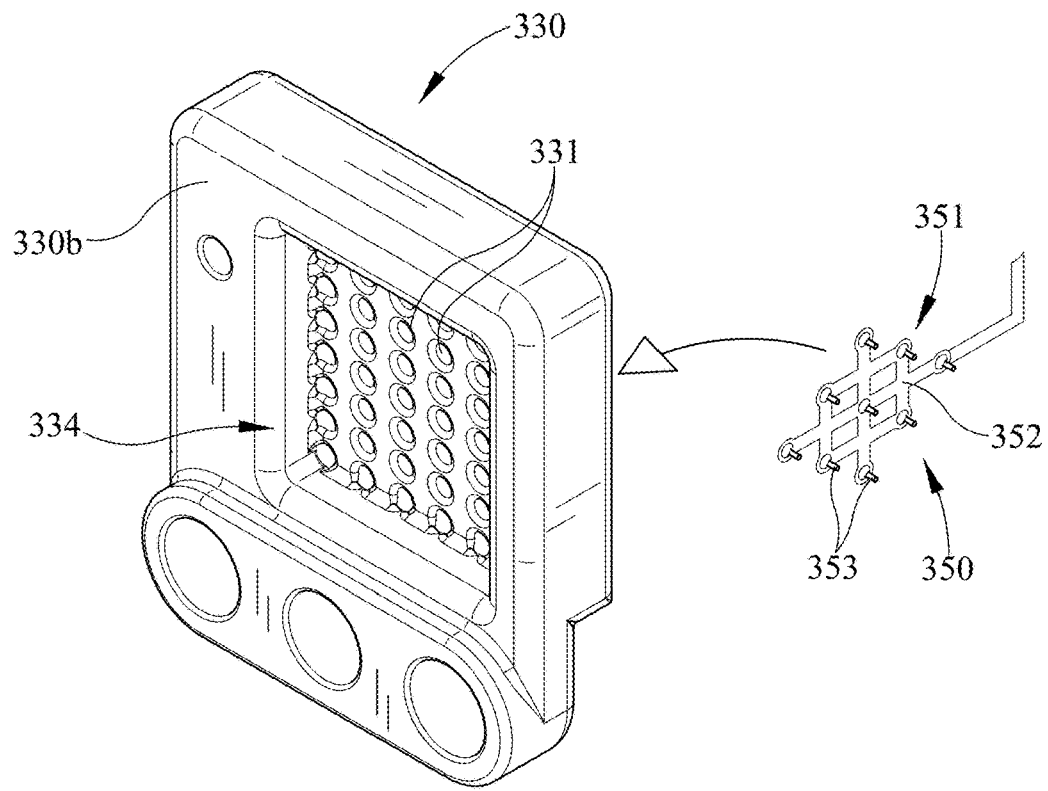
FIG. 15 is a perspective view of an embodiment of an outlet manifold of the bioreactor of FIG. 10 with the electrical stimulation device exploded therefrom.
Figure 16:
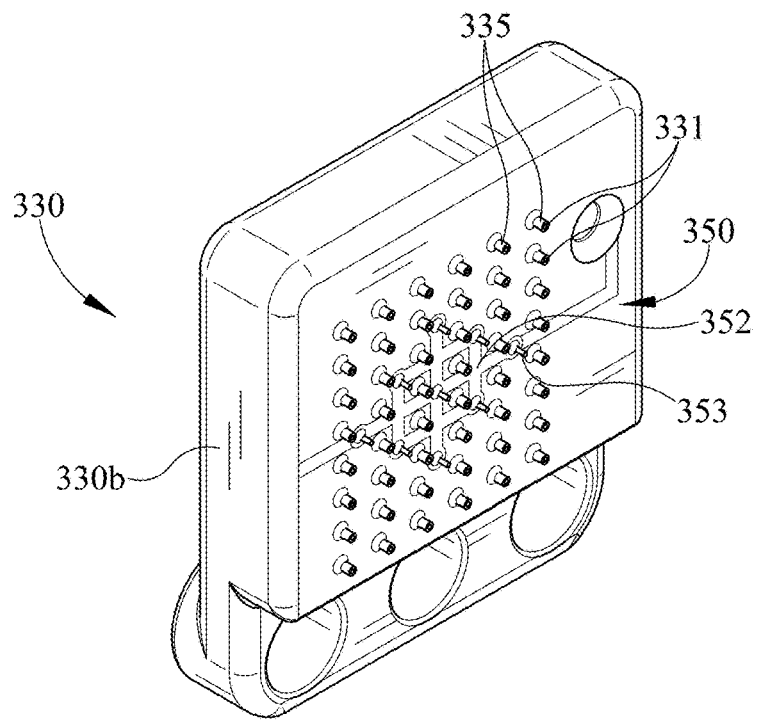
FIG. 16 is another perspective view of the outlet manifold of FIG. 15.
Figure 17:
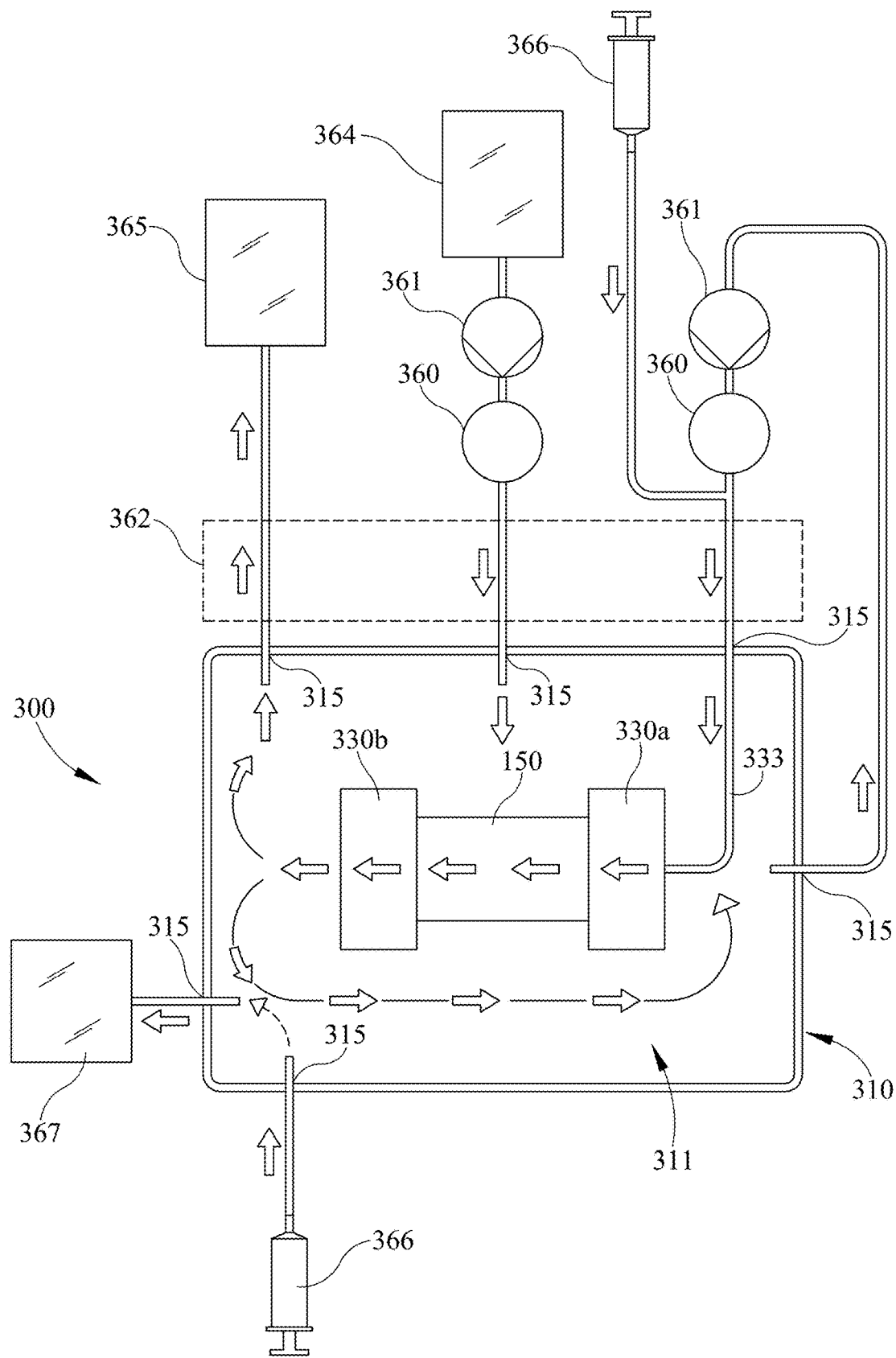
FIG. 17 is a schematic view of one embodiment of the fluid flow of the bioreactor of FIG. 10.

The manifold and/or ports may be subsequently engaged to the printed construct 150 after printing with the 3D bioprinter 2. Alternatively, the printed structure may be printed on one or more portions of one or more manifolds 330. One or more manifolds 330 (e.g. intake and/or outlet manifolds) may be positioned out of engagement with the 3D printed construct 150 and subsequently engaged with the 3D printed construct. Further, the manifolds 330 may be movable, positioned, or engaged with the printed construct manually and/or automatically by a drive mechanism or system. As shown in FIG. 11, the printed construct 150 may be printed within the bioreactor 300 (e.g. print platform 314 or volume 311) spaced away from one or more manifolds 330 in a disengaged position. As shown in FIG. 17, the manifolds 330 are positioned to an engaged position with the construct 150. One embodiment of a drive mechanism 341 (e.g. motor, belt, solenoid, etc.) that may be used to move (e.g. translate) the manifolds between the engaged and disengaged position with the construct 150 is shown in the figures. This drive mechanism 341 moves both manifolds into engagement with the 3D construct after printing. It should be understood that one manifold may be moved into engagement in some embodiments instead of a plurality of manifolds. The bioreactor 100 may include attachment mechanisms to secure the manifolds with the construct (e.g. during conditioning). The one or more manifolds or portions thereof (e.g. needles or ports) may include the attachment mechanism (not shown) such as, but is not limited to, chemical (e.g. adhesive) and/or mechanical attachments to the 3D printed construct. For example, an adhesive (e.g. bio adhesive) may be applied to or be present on the manifold or portions thereof to attach to the printed construct. Alternatively or in combination with the attachment mechanism of the bioreactor, the construct may include the attachment mechanism or portions thereof. For example, the printed tissue or material(s) thereof may include a bio adhesive to secure the interface of the manifold/ports and the 3D printed tissue. These attachment mechanisms may allow or assist in maintaining connectivity/communication (e.g. mechanical, electrical, and/or fluid communication) with the construct during mechanical manipulation or conditioning within the bioreactor (e.g. forces applied to the construct via one or more mechanical stimulation devices 340)

In some implementations, the bioreactor 300 may have one or more mechanical stimulation devices 340. The mechanical stimulation device 340 may be a variety of mechanisms or constructions manipulating the printed construct. The mechanical stimulation device may apply a variety of forces to the 3D construct in a variety of directions relative to the construct. As shown in the one embodiment, the mechanical stimulation device 340 may include a drive mechanism 341 embodiment having a motor 342 (e.g. stepper motor), drive belt 343, and a lead screw 344 manipulating the construct 150 in one or more directions. The drive mechanism 341 may move one or more of the manifolds 330 (e.g. intake and/or outlet manifold) at the same and/or different rates/times/durations. In the one embodiment shown, the drive mechanism 341 drives both manifolds 330a, 330b. In the one embodiment shown, the drive mechanism 341 may compress and/or extend the 3D printed construct 150 during conditioning with the manifolds. It should be understood that the same or different drive mechanism 341 that engages/disengages from the construct may apply the mechanical stimulation. As shown in the one embodiment, the drive mechanism 341 does both. The drive mechanism 341 applying the desired mechanical manipulation of the construct may also, in some embodiments, be configured to disengage from the 3D construct and/or engage with the 3D construct. The drive mechanism 341, in the one embodiment shown, drives the intake manifold 330a and the outlet manifold 330b towards each other (e.g. compression or compressed position) or away from each other (e.g. extending/extension or extended position) along a linear path or axis. Further, the manifolds 330 move at the same rate in the one embodiment shown. It should be understood that the manifolds may move at different rates, times, duration, and/or directions. For example, the mechanical stimulation device 340 (e.g. one or more of the manifolds) may apply compression, extending, and/or rotationally forces to the 3D construct in some embodiments. The drive mechanism or mechanical stimulation devices 340 may include a variety of seals 345 for sealingly engaging portions thereof (e.g. lead screw and/or guide pins 344) with the housing 310, volume 311, or other portions of the bioreactor.

In some implementations, the bioreactor 300 may have one or more electrical stimulation devices 350. The electrical stimulation device 350 may be a variety of constructions, quantities, shapes, sizes, and positions and still be in electrical communication with the 3D construct 150. In the one embodiment shown as shown more clearly in FIGS. 13-16, the one or more manifolds 330 may include one or more electrical stimulation devices 350. The electrical stimulation device 350 may include one or more conductive materials or members 351 engaging the 3D construct 150 to transfer electrical stimulation (e.g. voltage) through or into one of more portions of the construct. The electrical stimulation may be a variety of values, rates, sequences, durations, and engagement positions (e.g. contact surface area, penetration, etc.) with the construct to condition the corresponding tissue. In the one embodiment shown, each one of the intake manifold 330a and the outlet manifold 330b includes the conductive material 351 of the electrical stimulation device 350. Therefore the electrical stimulation may pass from the intake manifold 330a through the printed tissue 150 and continue to the outlet manifold 330b. One or more surfaces of the manifold 330 may include the conductive material 351. When the one or more manifolds 330 engage the 3D construct, the conductive material 351 may also engage the 3D construct. The manifolds 330 may be constructed of a variety of materials, although a ceramic may be used. The conductive material 351 may be an outer cover, exterior coating, or contact layer overlying the manifold (e.g. ceramic material) to contact the 3D construct. In the embodiment shown, the conductive material 351 may include a planar portion 352 and/or needles 353 (e.g. solid) projecting away from the manifold 330. The needles 353 may extend from the planar portions 352. These needles 353 may not define one or more ports. These needles or other structure may engage or penetrate the 3D construct at one or more depths, while the planar portion or other structure of the conductive material may engage the outer periphery of the 3D construct.

In some implementations, the bioreactor 300 may include one or more fluid traps 360 (e.g. trapping air or bubbles). The one or more air or fluid traps 360 may be in fluid communication with one or more of the fluid communications or conduits with or within the bioreactor 300 or housing 310. This removal of air may be in fluid flow recirculated/circulated, introduced to the bioreactor/printed tissue, and/or removed from the bioreactor or tissues located therein. The air traps 360 may reduce the air or bubbles generated during culturing, within the system/bioreactor, or circulated with other substances or media. The fluid or fluid pathways may be moved by one or more pumps 361 through and/or around the 3D printed construct. One or more valves 362 (e.g. a three way valve) and operating controls 363 may be used to circulate or move fluid relative to the bioreactor.

In some implementations, the bioreactor may include one or more feed/media bags 364 and/or pumps 361 in fluid communication with the construct 150, the housing 310, or portions of the bioreactor 300. As shown in FIG. 17, the one or more media bags 364 may supply fluid/media or be in fluid communication with the volume 311 of the housing 310. Moreover, the bioreactor 300 may include one or more valves 362 or controls 363 operating the flow with the media bag 364 and/or air trap 360. The air trap 360 may be in fluid communication with one or more media bags 364 and at least one port 315 of the housing 310. The media bags 364 may be detachable with the bioreactor for replacement with another media bag with similar media content or different media content.

In some implementations, the bioreactor 300 may include one or more waste bags 365 and/or pumps 361 in fluid communication with the construct 150, housing 310, or portions of the bioreactor 300. As shown in FIG. 17, the one or more waste bags 365 may be in fluid communication with the volume 311 of the housing 310. Moreover, the bioreactor may include one or more valves 362 or controls 363 operating the fluid flow with the volume 311 of the housing 310 or portions of the bioreactor 300. The waste bag 365 may be in downstream fluid communication with one or more ports 315 of the housing 310. The waste bags 365 may be detachable with the bioreactor for replacement with another waste bag.

In the embodiment shown, the bioreactor 300 may include one or more air traps 360 in fluid communication with one or more ports 331 engaging the 3D printed construct 150, media bags, manifolds 330 (e.g. intake manifold), and/or other portions of the bioreactor 300. In some embodiments as shown in FIG. 17, one or more pumps 361 may be used to circulate media/substrate or fluid through one or more manifolds 330 and/or the printed tissue 150. Moreover, the circulated fluid or media may be pumped into, through, and/or from the volume 311 of the housing 310. As shown in the one embodiment in FIGS. 13, 14, 14a, and 17, the recirculated fluid path may extend at least from the air trap 360 through the port 315 of the housing 310 and divides from the supply conduit 333 into the one or more channels 332 of the intake manifold 330a to exit through the intake ports 331. As further shown in FIG. 17, upon passing from the intake manifold ports 331, the fluid may pass through the 3D printed construct 150 (e.g. vessel structure) before exiting through the ports 331 and/or outlet manifold 330b (e.g. chamber 334) and into the volume 311 of the housing 310. The fluid within the housing 310 may then exit through another port 315 of the housing 310 and continue back to the air trap 360 via the pump 361. Moreover, the bioreactor may include one or more valves 362, pumps 361, or controls 363 operating the flow with the 3D printed construct 150, manifolds 330, volume 311, and/or ports 331.

In some implementation, the bioreactor 300 or portions thereof may be primed with media or desired fluid. Priming one or more portions of the bioreactor may reduce the air circulated and/or remove air from one or more portions of the bioreactor. In the one embodiment shown in FIG. 17, the volume 311 defined by the housing 310 may be primed manually with a fluid or media (e.g. saline or desired media)

manually with a syringe 366 and/or an air waste bag 367 attached thereto. Alternatively, a media bag 364 may be attached to the housing and pumped therein to fill up the volume 311. Moreover, in some embodiments as shown in FIG. 17, the supply conduit 333 to the intake manifold 330a may be primed with a syringe 366 with a fluid or media (e.g. saline or other desired media) via an input with the recirculation pathway. The priming through the supply conduit 333, may remove air or prime the manifold (e.g. ports or intake manifold). For example, the intake manifold may be primed before engaging the construct 150 to reduce or eliminate air delivered to the construct.

In the embodiment shown, the lid 312 and base 313 may also have one or more interior surfaces defining the volume 311 therein constructed to reduce the trapping of air and/or increase the removal of air. The interior surfaces defining the inner periphery of the housing 310 or volume 311 may be rounded with large radii and/or have chamfered edges. The chamfered or rounded edges may be used on one or more portions or surfaces within the bioreactor (e.g. lid, base, manifolds, print platform, etc.).

Although not shown, the bioreactor 300 may include one or more light sources. The light sources may illuminate the contents or volume of the bioreactor or portions of the bioreactor to aid in visual monitoring (e.g. monitoring device 301).

In use, the bioreactor 300 may include a cassette or cassette housing 316. The cassette 316 may include a sealable lid 317 as shown in FIG. 10. The cassette 316 and/or bioreactor 300 may be engaged with the 3D bioprinter 2 and/or biomanufacturing facility 1 within the reduced gravity environment 30 with the housing lid 312 and/or cassette 316 (e.g. lid 317) opened. One or more 3D constructs 150 may be printed into the one or more bioreactors 300 and/or within the opened housing 310. For example, the printed 3D construct may be printed adjacent to or on the print platform 314. The intake manifold 330a and/or ports 331 may be primed or air is removed from one or more fluid lines or conduits. This priming or evacuation of air from the intake manifold 330a or ports 331 may be from a bypass (e.g. via a syringe 366) and/or by pumping media or substrate (e.g. saline) through the recirculation lines/pump. The manifold 330 and/or ports 331 of one or both of the intake/outlet manifolds 330a, 330b may be in the disengaged position from the printed tissue 150 and moved towards and engages the printed tissue in the engaged position. The perfusion ports 331 (e.g. needles), electrical stimulation device 350 (e.g. needles and/or planar portions), and/or mechanical stimulation devices 340 may engage the printed tissue in at least one position (e.g. engaged position) of the one or more manifolds. Attachment mechanisms (e.g. adhesive and/or mechanical attachments) may engage one or more portions of the manifolds 330 with one or more portions of the 3D construct 150. For example, mechanical and/or chemical attachments (e.g. adhesives) may engage the ports 331 with vessel structure of the printed tissue 150. Further, the electrical/mechanical stimulation devices may be engaged by mechanical/chemical attachments. The lid 312 of the housing 310 may be closed and/or sealed with one or more locking mechanisms 302 (e.g. clamps). One or more media bags 364 may be fluidly attached the housing 310 or portions of the bioreactor 300. One or more media waste bags 365 may be fluidly attached to the housing 310 or portions of the bioreactor 300. One or more air waste bags 367 may be fluidly attached to the housing 310 or portions of the bioreactor 300. With the volume 311 of the housing 310 sealed, the air within the volume may be evacuated or removed to the air waste bags 367. The air may be manually removed via a syringe 366 by introducing saline or media into the housing 310 to push air out of the volume 311 and into the air waste bag 367. Alternatively, and or in combination with the manual evacuation, the air from the volume 311 may be pushed out of the housing 310 by pumping media in from one or more media bags 364. The cassette 316 containing the bioreactor housing 310 may be closed/sealed. At some point during use, the cassette 316 or bioreactor 300 may be removed from the 3D bioprinter 2.

In use, the 3D printed construct 150 may be conditioned or cultured within the reduced gravity environment 30. The recirculation of media, addition/removal of media, perfusion stimulation, collection and/or removal of waste, and/or removal of air/bubbles, the electrical stimulation, and/or mechanical stimulation within the one or more bioreactors may be operated by one or more operating controls 363. Alternatively, or in combination thereof, one or more of these steps or operations may be completed manually. Air may be removed from the circulation of media or fluid flow within the bioreactor or to the manifolds 330/ports 331. Air may be removed from media introduced from the media bag 364 to the housing 310. When needed, waste may be removed from the housing. Additional media or supplemental media may be added to the bioreactor 300 at various stages or conditions of the 3D construct. The 3D construct may have one or more perfusion ports providing media thereto. One or more electrical stimulations may be provided to the 3D construct. One or more mechanical stimulations (e.g. compression, extending, and/or rotational forces) may be provided during the conditioning of the 3D construct. The bioreactor may monitor the 3D construct and/or provide the perfusions and/or electrical/mechanical stimulations when needed for conditioning. Once a bioreactor and/or cassette is removed from the 3D printer, another bioreactor may be engaged or positioned with the 3D bioprinter and begin printing another 3D tissue (e.g. the same or different tissue).

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It is to be understood that the embodiments are not limited in its application to the details of construction and the arrangement of components set forth in the description or illustrated in the drawings. The invention is capable of other embodiments and of being practiced or of being carried out in various ways. Unless limited otherwise, the terms "connected," "coupled," "in communication with," and "mounted," and variations thereof herein are used broadly and encompass direct and indirect connections, couplings, and mountings. In addition, the terms "connected" and "coupled" and variations thereof are not restricted to physical or mechanical connections or couplings.

The foregoing description of several embodiments of the invention has been presented for purposes of illustration. It is not intended to be exhaustive or to limit the invention to the precise steps and/or forms disclosed, and obviously many modifications and variations are possible in light of the above teaching.

What is claimed is:

1. A bioreactor for receiving a printed tissue comprising:
   a housing having one or more manifolds therein adapted to engage a printed tissue;
   the one or more manifolds having each one of
   a plurality of perfusion ports in fluid communication with a printed tissue;
   one or more electrical stimulation devices; and
   a mechanical stimulation device connected thereto,
   wherein at least one of the one or more manifolds contains the plurality of perfusion ports defined by one or more needles; and
   wherein the one or more electrical stimulation devices is an exterior coating to the one or more manifolds.

2. The bioreactor of claim 1 further comprising a print platform.

3. The bioreactor of claim 1 wherein the mechanical stimulation device moves the one or more manifolds between a compressed position and an extended position.

4. The bioreactor of claim 1 wherein the exterior coating includes one or more needles.

5. The bioreactor of claim 1 wherein the one or more manifolds include an intake manifold and an outlet manifold.

6. The bioreactor of claim 5 wherein at least one of the intake manifold and the outlet manifold includes one or more needles defining the plurality of perfusion ports.

7. The bioreactor of claim 5 wherein at least one of the intake manifold and the outlet manifold includes one or more channels in communication with the plurality of perfusion ports.

8. The bioreactor of claim 5 wherein at least one of the intake manifold and the outlet manifold are moveable relative to each other.

9. The bioreactor of claim 1 wherein the one or more electrical stimulation devices include a conductive material positioned on one or more surfaces of the one or more manifolds.

10. The bioreactor of claim 9 wherein the conductive material includes one or more needles projecting and adapted to engage a printed tissue.

11. The bioreactor of claim 1 wherein the mechanical stimulation device includes a drive mechanism moving at least one of the one or more manifolds.

12. The bioreactor of claim 1 further comprising one or more air traps in fluid communication with the plurality of perfusion ports.

13. The bioreactor of claim 1 further comprising one or more detachable feed bags and waste bags.

\* \* \* \* \*